(12) United States Patent
Singhvi et al.

(10) Patent No.: US 7,993,905 B2
(45) Date of Patent: *Aug. 9, 2011

(54) DEVICE CONTAINING CYTOPHILIC ISLANDS THAT ADHERE CELLS SEPARATED BY CYTOPHOBIC REGIONS

(75) Inventors: Rahul Singhvi, Potomac, MD (US); Amit Kumar, San Jose, CA (US); George M. Whitesides, Newton, MA (US); Donald E. Ingber, Boston, MA (US); Gabriel P. Lopez, Albuquerque, NM (US); Daniel I. C. Wang, Cambridge, MA (US); Gregory Stephanopoulos, Winchester, MA (US)

(73) Assignees: President and Fellows of Harvard College, Cambridge, MA (US); Massachusetts Institute of Technology, Cambridge, MA (US); Children's Medical Center Corporation, Boston, MA (US)

( * ) Notice: Subject to any disclaimer, the term of this patent is extended or adjusted under 35 U.S.C. 154(b) by 305 days.

This patent is subject to a terminal disclaimer.

(21) Appl. No.: 12/166,287

(22) Filed: Jul. 1, 2008

(65) Prior Publication Data
US 2009/0011493 A1    Jan. 8, 2009

Related U.S. Application Data

(63) Continuation of application No. 11/331,849, filed on Jan. 13, 2006, now Pat. No. 7,410,791, which is a continuation of application No. 10/032,280, filed on Dec. 21, 2001, now Pat. No. 7,067,306, which is a continuation of application No. 09/373,334, filed on Aug. 12, 1999, now Pat. No. 6,368,838, which is a continuation of application No. 08/951,886, filed on Oct. 16, 1997, now Pat. No. 5,976,826, which is a continuation of application No. 08/659,537, filed on Jun. 6, 1996, now Pat. No. 5,776,748, which is a continuation of application No. 08/131,838, filed on Oct. 4, 1993, now abandoned.

(51) Int. Cl.
*C12N 1/00* (2006.01)
*C12N 11/00* (2006.01)
*C12N 11/08* (2006.01)

(52) U.S. Cl. ......... 435/283.1; 435/30; 435/34; 435/177; 435/180; 435/243; 435/252.1; 435/252.4; 435/253.6; 435/254.1; 435/255.1; 435/256.8; 435/395; 435/402

(58) Field of Classification Search .................. None
See application file for complete search history.

(56) References Cited

U.S. PATENT DOCUMENTS

| | | |
|---|---|---|
| 2,905,539 A | 9/1959 | Bowerman |
| 3,497,377 A | 2/1970 | Allingham |
| 3,559,570 A | 2/1971 | Martel et al. |
| 3,641,354 A | 2/1972 | DeMent |
| 3,716,359 A | 2/1973 | Sheridon |
| 3,873,357 A | 3/1975 | Lando |
| 4,011,009 A | 3/1977 | Lama et al. |
| 4,173,075 A | 11/1979 | Stewart |
| 4,274,706 A | 6/1981 | Tangonan |
| 4,279,852 A | 7/1981 | Engelmann |
| 4,325,779 A | 4/1982 | Rossetti |
| 4,330,175 A | 5/1982 | Fujii et al. |
| 4,382,657 A | 5/1983 | Lemaitre |
| 4,477,158 A | 10/1984 | Pollock et al. |
| 4,512,848 A | 4/1985 | Deckman et al. |
| 4,528,260 A | 7/1985 | Kane |
| 4,582,566 A | 4/1986 | Grey |
| 4,587,213 A | 5/1986 | Malecki |
| 4,690,715 A | 9/1987 | Allara et al. |
| 4,728,591 A | 3/1988 | Clark et al. |
| 4,731,155 A | 3/1988 | Napoli et al. |
| 4,735,890 A | 4/1988 | Nakane |
| 4,802,951 A | 2/1989 | Clark et al. |
| 4,818,336 A | 4/1989 | Rossetti |
| 4,842,633 A | 6/1989 | Kuribayashi et al. |
| 4,897,325 A | 1/1990 | Akkapeddi et al. |
| 4,999,489 A | 3/1991 | Huggins |
| RE33,581 E | 4/1991 | Nicoli et al. |
| 5,009,708 A | 4/1991 | Grünwald et al. |
| 5,018,829 A | 5/1991 | Ogawa |
| 5,020,879 A | 6/1991 | Kuzuta et al. |
| 5,032,216 A | 7/1991 | Felten |
| 5,079,600 A | 1/1992 | Schnur et al. |
| 5,106,182 A | 4/1992 | Briggs et al. |

(Continued)

FOREIGN PATENT DOCUMENTS

JP    58150148    9/1983

(Continued)

OTHER PUBLICATIONS

Abbott, et al., "Manipulation of the Wettability of Surfaces on the 0.1-to 1-Micrometer Scale Through Micromachining and Molecular Self-Assembly", Science 257, pp. 1380-1382 (Sep. 4, 1992).

Abbott, et al., "Potential-Dependent Wetting of Aqueous Solutions on Self-Assembled Monolayers Formed from 15-(Ferrocenylcarbonyl)pentadecanethiol on Gold", Langmuir 10, pp. 1493-1497, May 20, 1994.

Abbott, Nicholas L., et al., "Active Control of Wetting Using Applied Electrical Potentials and Self-Assembled Assembled Monolayers", Langmuir, vol. 11, No. 1, pp. 16-18 (1995).

Bergveld, "The Challenge of Developing µTAS", Micro Total Analysis Systems, Proceedings of the µTAS '94 Workshop, Nov. 21-22, 1994, Kluwer Academic Publishers, pp. 1-4, 1995.

(Continued)

*Primary Examiner* — Debbie K Ware
(74) *Attorney, Agent, or Firm* — Wolf, Greenfield & Sacks, P.C.

(57) ABSTRACT

The invention provides a device for adhering cells in a specific and predetermined position, and associated methods. The device includes a plate defining a surface and a plurality of cytophilic islands that adhere cells, isolated by cytophobic regions to which cells do not adhere, contiguous with the cytophilic islands. The islands or the regions or both may be formed of a self-assembled monolayer (SAM).

19 Claims, 1 Drawing Sheet

U.S. PATENT DOCUMENTS

| | | | |
|---|---|---|---|
| 5,143,854 | A | 9/1992 | Pirrung et al. |
| 5,172,171 | A | 12/1992 | Beaudet et al. |
| 5,202,227 | A | 4/1993 | Matsuda et al. |
| 5,255,273 | A | 10/1993 | Nilsson et al. |
| 5,259,926 | A | 11/1993 | Kuwabara et al. |
| 5,294,369 | A | 3/1994 | Shigekawa et al. |
| 5,315,436 | A | 5/1994 | Lowenhar et al. |
| 5,324,591 | A | 6/1994 | Georgei, Jr. et al. |
| 5,512,131 | A | 4/1996 | Kumar et al. |
| 5,776,748 | A | 7/1998 | Singhvi et al. |
| 5,900,160 | A | 5/1999 | Whitesides et al. |
| 5,928,880 | A | 7/1999 | Wilding et al. |
| 5,937,758 | A | 8/1999 | Maracas et al. |
| 5,955,029 | A | 9/1999 | Wilding et al. |
| 5,976,826 | A | 11/1999 | Singhvi et al. |
| 6,020,047 | A | 2/2000 | Everhart |
| 6,103,479 | A | 8/2000 | Taylor |
| 6,167,910 | B1 | 1/2001 | Chow |
| 6,180,239 | B1 | 1/2001 | Whitesides et al. |
| 6,184,029 | B1 | 2/2001 | Wilding et al. |
| 6,197,515 | B1 | 3/2001 | Bamdad et al. |
| 6,321,791 | B1 | 11/2001 | Chow |
| 6,329,209 | B1 | 12/2001 | Wagner et al. |
| 6,334,301 | B1 | 1/2002 | Otsap et al. |
| 6,355,198 | B1 | 3/2002 | Kim et al. |
| 6,368,838 | B1 | 4/2002 | Singhvi et al. |
| 6,368,877 | B1 | 4/2002 | Zhang et al. |
| 6,413,587 | B1 | 7/2002 | Hawker et al. |
| 6,518,168 | B1 | 2/2003 | Clem et al. |
| 6,719,868 | B1 | 4/2004 | Schueller et al. |
| 6,776,094 | B1 | 8/2004 | Whitesides et al. |
| 7,067,306 | B2 | 6/2006 | Singhvi et al. |
| 7,410,791 | B2 | 8/2008 | Singhvi et al. |
| 2002/0071943 | A1 | 6/2002 | Hawker et al. |
| 2002/0072074 | A1 | 6/2002 | Zhang et al. |
| 2002/0094572 | A1 | 7/2002 | Singhvi et al. |
| 2004/0023414 | A1 | 2/2004 | Zhang et al. |

FOREIGN PATENT DOCUMENTS

| | | |
|---|---|---|
| JP | 2140702 | 5/1990 |
| JP | 2165933 | 6/1990 |
| JP | 2210302 | 8/1990 |
| WO | WO 95/12480 | 5/1995 |
| WO | WO 97/07429 | 2/1997 |
| WO | WO 97/33737 | 9/1997 |
| WO | WO 99/54786 | 10/1999 |
| WO | WO 01/03208 A1 | 1/2001 |
| WO | WO 01/89787 A2 | 11/2001 |
| WO | WO 01/89788 A2 | 11/2001 |

OTHER PUBLICATIONS

Bhatia, Suresh K., et al., "Fabrication of Surfaces Resistant to Protein Adsorption and Application to Two-Dimensional Protein Patterning", Anal. Biochem., vol. 208, pp. 197-205 (1993).

Biebuyck, et al., "Self-Organization of Organic Liquids on Patterned Self-Assembled Monolayers of Alkanethiolates on Gold", Langmuir 10, pp. 2790-2793 (Mar. 14, 1994).

Blankenstein & Larsen, "Modular concept of a laboratory on a chip for chemical and biochemical analysis," Biosensors & Bioelectronics, vol. 13, No. 3-4, pp. 427-438, 1998.

Bloomstein & Ehrlich, "Laser-Chemical 3-D Micromachining," Mat. Res. Soc. Symp. Proc., vol. 282, pp. 165-171, 1993.

Bloomstein & Ehrlich, "Laser-chemical three-dimensional writing for microelectromechanics and application to standard-cell microfluidics," J. Vac. Sci. Tehcnolo. B, vol. 10, No. 6, pp. 2671-2674, Nov./Dec. 1992.

Bloomstein & Ehrlich, "Laser-Chemical Three-Dimensional Writing of Multimaterial Structures for Microelectromechanics," IEEE, pp. 202-203, 1991.

Britland, et al., "Micropatterned Substratum Adhesiveness: A Model for Morphogenetic Cues Controlling Cell Behavior", Exper. Cell Research 198, pp. 124-129 (Jan. 20, 1992).

Calvert, Jeffrey M., Calvert et al., "Deep Ultraviolet Lithography of Monolayer Films with Selective Electroless Metallization", J. Electrochem. Soc., vol. 139, No. 6, pp. 1677-1680 (1982).

Calvert, Jeffrey M., et al., "Deep ultraviolet patterning of monlayer films for high resolution lithography", J. Vac. Sci. Technol. B, vol. 9, No. 6, pp. 3447-3450 (1991).

Calvert, Jeffrey M., et al., "New Surface Imaging Techniques for Sub-0.5 Micrometer Optical Lithography", Solid State Technology, pp. 77-82 (1991).

Chehroudi, B., T.R.L. Gould and D.M. Brunette, "Titanium-coated Micromachined Grooves of Different Dimensions Affect Epithelial and Connective-Tissue Cells Differently in Vivo", Journal of Biomedical Materials Research, 24:1203-1219, 1990.

Chiu, et al., "Patterned deposition of cells and proteins onto surfaces by using three dimensional microfluidic system", Proceedings of the Nationa; Academy of Sciences of USA, vol. 97, No. 6, pp. 2408-2413, Mar. 14, 2000.

Clark, P., P. Connolly, A.S.G. Curtis, J.A.T. Dow and C.D.W. Wilkinson, "Topographical Control of Cell Behaviour I. Simple Step Cues", Development, 99:439-448, 1987.

Cromie, "Self-Assembling Molecules Manipulated by Chemists", Harvard's Gazette (Jul. 9, 1993).

Dobisz, E.A., et al., "Self-Assembled Monolayer Films for Nanofabrication," Mat. Res. Soc Symp. Proc., vol. 380, 1995.

Dressick, Walter J., et al., "Photopatterning and Selective Electroless Metallization of Surface-Attached Ligands", Chem. Mater., vol. 5, No. 2, pp. 148-150 (1993).

Duffy, et al., "Rapid Prototyping of Microfluidic Systems in Poly(dimethylsiloxane)," Analytical Chemistry, vol. 70, No. 23, pp. 4974-4985, 1998.

Dulcey, et al., "Deep UV Photochemistry of Chemisorbed Monolayers: Patterned Coplanar Molecular Assemblies", Science 252, pp. 551-554 (Apr. 26, 1991).

Dunn, G.A. and A.F. Brown, Alignment of Fibroblasts on Grooved Surfaces Described by a Simple Geometric Transformation:, J. Cell. Sci., 83:313-340, 1986.

Fettinger, et al., "Stacked modules for micro flow systems in chemical analysis: concept and studies using an enlarged model," Sensors and Actuators B, vol. 17, pp. 19-25, 1993.

Fluitman, et al., "Micromechanical Components for μTAS," Micro Total Analysis Systems, Proceedings of the μTAS '94 Workshop, Nov. 21-22, 1994, Kluwer Academic Publishers, pp. 73-83, 1995.

González, et al., "MicroJoinery: concept, definition, and application to microsystem development," Sensors and Actuators A, vol. 66, pp. 315-332, 1998.

Gorman, Christopher B., et al., "Control of the Shape of Liquid Lenses on a Modified Gold Surface Using an Applied Electrical Potential across a Self-Assembled Monolayer", Langmuir, vol. 11, No. 6, pp. 2242-2246 (1995).

Gorman, Christopher B., et al., "Fabrication of Patterned, Electrically Conducting Polypyrrole Using a Self-Assembled Monolayer: A Route to All-Organic Circuits", Chem. Mater., vol. 7, No. 3, pp. 526-529 (1995).

Gorman, et al., "Use of a Patterned Self-Assembled Monolayer to Control the Formation of a Liquid Resist Pattern on a Gold Surface", Chem. Mater. 7, pp. 252-254 (Feb. 15, 1995).

Guérin, et al., "Simple and Low Cost Fabrication of Embedded Micro-Channels by Using a New Thick-Film Photoplastic," 1997 International Conference on Solid-State Sensors and Actuators, Jun. 18-19, 1997, IEEE, pp. 1419-1422, 1997.

Harris, A., "Behavior of Cultured Cells on Substrata of Variable Adhesiveness", Experimental Cell Research, 77:285-297, 1973.

Hartney, M. A., et al., "Silylation of focused ion beam exposed resists", Appl. Phys. Lett., vol. 59, No. 4, pp. 485-487 (1991).

Huber, et al., "Toroidal grating obtained on an elastic substrate", Applied Optics 20(12), pp. 2139-2142, Jun. 15, 1981.

Huber, M.C.E., et al., "Toroidal grating obtained on an elastic substrate", Applied Optics, vol. 20, No. 12, pp. 2139-2142 (1981).

Ichinose, Nobuyuki, "Immobilization of Protein on Micropatterns by the Use of Photoremovable Activated Ester", Chemistry Letters, pp. 237-238 (1995).

Ikuta, et al., "Three Dimensional Micro Integrated Fluid Systems (MIFS) Fabricated by Stereo Lithography," IEEE, pp. 1-6, 1994.

Ingber, D.E., "Fibronectin Controls Capillary Endothelial Cell Growth by Modulating Cell Shape", Proc. Nat. Acad. Sci. (U.S.A.), 87:3579-3583, 1990.

Inoue, T., J.E. Cox, R.M. Pilliar and A.H. Melcher, "Effect of the Surface Geometry of Smooth and Porous-coated Titanium Alloy on the Orientation of Fibroblasts in Vitro", Journal of Biomedical Materials Research, 21:107-126, 1987.

Ireland, G.W., P. Dopping-Hepenstal, P. Jordan and C. O'Neill, "Effect of Patterned Surfaces of Adhesive Islands on the Shape, Cytoskeleton, Adhesion and Behaviour of Swiss Mouse 3T3 Fibroblasts", J. Cell. Sci. Suppl., 8:19-33, 1987.

Ireland, et al., "Limitation of Substratum Size Alters Cyto-Skeletal Organization and Behaviour of Swiss 3T3 Fibroblasts", Cell Bio. Int'l Reports 13, pp. 781-790 (Sep. 1989).

Jackman, et al., "Design and Fabrication of Topologically Complex, Three-Dimensional Microstructures," Science, vol. 280, pp. 2089-2091, Jun. 1998.

Jacobsen, et al., "Design, Analysis, and Experimental Results for the Wobble Motor: An Eccentric-Motion Electrostatic Microactuator", SPIE 1167, pp. 122-136 (1989).

Jacobsen, et al., "Fabrication of Micro-Structures Using Non-Planar Lithography (NPL)", Proceedings, IEEE; Micro Electro Mechanical Systems, An Investigation of Micro Structures, Sensors, Actuators, Machines and Robots, Nara, Japan, Jan. 30-Feb. 2, 1991.

Jacobsen, et al., "The Wobble Motor: Design Fabrication and Testing of an Eccentric-Motion Electrostatic Microactuator", IEEE, pp. 1536-1546, (1989).

Jo, et al., "Three-Dimensional Micro-Channel Fabrication in Polydimethylsiloxane (PDMS) Elastomer," Journal of Microelectromechanical Systems, vol. 9, No. 1, pp. 76-81, Mar. 2000.

Jo & Beebe, "Fabrication of Three-Dimensional Microfluidic Systems by Stacking Molded Polydimethylsiloxane (PDMS) Layers," SPIE Conference on Microfluidic Devices and Systems II, SPIE, vol. 3877, pp. 222-229, Sep. 1999.

Kang, Doris, et al., "Patterned Functionalization of Gold and Single Crystal Silicon via Photochemical Reaction of Surface-Confined Derivatives of (.eta..sup.5—C.sub.5H.sub.5)Mn(CO).sub.3", Langmuir, vol. 7, No. 10, pp. 2169-2174 (1991).

Kenis, et al., Science, vol. 285, Jul. 2, 1999, 1183-1185.

Kim, et al., Combining Patterned Self-Assembled Monolayers of Alkanethiolates on Gold with Anisotropic Etching of Silicon to Generate Controlled Surface Morphologies, J. Electrochem. Soc. 142(2), pp. 628-633 (Feb. 1995).

Kleinfeld, et al., "Controlled Outgrowth of Dissociated Neurons on Patterned Substrates", Journal of Neuroscience, 8, pp. 4098-4120 (Nov. 1988).

Koloski, Timothy S., et al., "Nucleophilic Displacement Reactions at Benzyl Halide Self-Assembled Monolayer Film Surfaces", Langmuir, vol. 10, No. 9, pp. 3122-3133 (1994).

Kumar, Amit, et al., "Features of gold having micrometer to centimeter dimensions can be formed through a combination of stamping with an elastomeric stamp and an alkanethiol 'ink' followed by chemical etching", Appl. Phys. Lett., vol. 63, No. 14. pp. 2002-2004 (1993).

Kumar, Amit, et al., "Patterning Self-Assembled Monolayers: Applications in Materials Science", American Chemical Chemical Society, Langmuir Vo. 10, No. 5 (1994), pp. 1498-1511.

Kumar, et al., "Patterning Self-Assembled Monolayers: Applications in Materials Science", Langmuir 10, pp. 1498-1511 (May 20, 1994).

Kumar, et al., "The Use of Self-Assembled Monolayers and a Selective Etch to Generate Patterned Gold Features", Amer. Chem. Society. 14, pp. 9188-9189 (Nov. 4, 1992).

Kunz, et al., "Applications of lasers in microelectronics and micromechanics," Applied Surface Science, vol. 79/80, pp. 12-24, 1994.

Labinis, et al., "Comparison of the Structures and Wetting Properties of Self-Assembled Monolayers of n-Alkanethiols on the Coinage Metal Surfaces, Cu, Ag, Au.sup.1", Amer. Chem. Soc. 113(19), pp. 7152-7167 (Jan. 14, 1991).

Lammerink et al., "Modular Concept for Fluid Handling Systems, A demonstrator Micro Analysis System," IEEE, pp. 389-394, 1996.

Larsson, et al., "Silicon Based Replication Technology of 3D-Microstructures by Conventional CD-Injection Molding Techniques," 1997 International Conference on Solid-State Sensors and Actuators, Jun. 16-19, 1997, IEEE, pp. 1415-1418, 1997.

Lercel, M. J., et al., "Pattern transfer of electron beam modified self-assembled monolayers for high-resolution lithography", J. Vac. Sci. Tecnol. B, vol. 13, No. 3, pp. 1139-1143 (1995).

Lercel, Microelect Eng, 27:43-46 (1995).

Lopez, et al., "Convenient Methods for Patterning the Adhesion of Mammalian Cells to Surfaces Using Self-Assembled Monolayers of Alkanethiolates on Gold", Amer. Chemical Society 115, pp. 5877-5878 (Feb. 22, 1993).

Lopez, et al., "Imaging of Features on Surfaces by Condensation Figures", Science 260, pp. 647-649 (Apr. 30, 1993).

Matsuda, et al., "Development of Micropatterning Technology for Cultured Cells", Trans. Am. Soc. Artif. Intern Organs 36 (1990).

McGovern, et al., "Role of Solvent on the Silanization of Glass with Octadecyltrichlorosilane", Langmuir, Jun. 20, 1994, vol. 10, No. 10, pp. 3607-3614.

Mensinger, et al., "Microreactor with Integrated Static Mixer and Analysis System," Micro Total Analysis Systems, Proceedings of the μTAS '94 Workshop, Nov. 21-22, 1994, Kluwer Academic Publishers, pp. 237-243, 1995.

Moffat, T.P., et al., "Patterned Metal Electrodeposition Using an Alkanethiolate Mask," J. Electrochem. Soc., vol. 142, No. 11, Nov. 1995.

Nassuphis, et al., "Three-dimensional laser direct writing: Applications to multichip modules," J. Vac. Sci. Technol. B, vol. 12, No. 6, pp. 3294-3299, Nov./Dec. 1994.

O'Neill, et al., "Narrow Linear Strips of Adhesive Substratum are Powerful Inducers of Both Growth and Focal Contact Area", Cell Science 95, pp. 577-586 (Jan. 2, 1990).

O'Neill, C., P. Jordan, and G. Ireland, "Evidence for Two Distinct Mechanisms of Anchorage Stimulation in Freshly Explanted and 3T3 Swiss Mouse Fibroblasts", Cell, 44:489-496, 1986.

Parikh, et al., "An Intrinsic Relationship Between Molecular Structure in Self-Assembled n-Alkylsiloxane Monolayers and Deposition Temperature", J. Phys. Chem., May 3, 1995, vol. 98, No. 31, pp. 7577-7590.

Ponten, et al., "Proliferation Control in Cloned Normal and Malignant Human Cells", Exper. Cell Research, pp. 367-375 (May 12, 1980).

Poplawski, et al., "A Simple Package Process for Chemical Sensors," Solid-State Sensor and Actuator Workshop, Jun. 13-16, 1994, TRF, pp. 25-28, 1994.

Potochnik, Stephen J., et al., "Selective Copper Chemical Vapor Deposition Using Pd-Activated Organosilane Films", Langmuir, vol. 11, No. 6, pp. 1841-1845 (1995).

Pritchard, David John, et al., "Micron-Scale Patterning of Biological Molecules", Angew. Chem. Int. Ed. Engl. Engl., vol. 34, No. 1, pp. 91-93 (1995).

Rozsnyai, Lawrence F., et al., "Selective Electrochemical Deposition of Polyaniline via Photopatterning of a Monolayer-Modified Substrate", J. Am. Chem. Soc., vol. 116, No. 13, pp. 5993-5994 (1994).

Schoer, J.K., et al., "Scanning Probe Lithography," Langmuir, vol. 10, No. 3, pp. 615-618, 1994. (Abstract).

Schomburg, et al., "Components for Microfluidic Handling Modules," Micro Total Analysis Systems, Proceedings of the μTAS '94 Workshop, Nov. 21-22, 1994, Kluwer Academic Publishers, pp. 1-4, 1995.

Singhvi, et al., "Engineering Cell Shape and Function", Science 264, p. 696 (Apr. 29, 1994).

Sondag-Huethorst, J.A.M., et al., "Generation of electrochemically deposited metal patterns by means of electron beam (nano)lithography of self-assembled monolayer resists", Appl. Phys. Lett., vol. 64, No. 3, pp. 285-287 (1994).

Spinke, et al., "Molecular Recognition at Self-Assembled Monolayers: Optimization of Surface Functionalization", J. Chem. Phys., vol. 99, No. 9, pp. 7012-7019, Nov. 1, 1993.

Stenger, David A., "Coplanar Molecular Assemblies of Amino- and Perfluorinated Alkylsilanes: Characterization and Geometric Definition of Mammalian Cell Adhesion and Growth", J. Am. Chem. Soc., vol. 114, No. 22, pp. 8435-8442 (1992).

Takayama, et al., Proc. Natl. Acad. Sci. USA, vol. 96, May 1999, pp. 5545-5548.

Tarlov, et al., "UV Photopatterning of Alkanethiolate Monolayers Self-Assembied on Gold and Silver", Am. Chem. Soc. 115 (Apr. 13, 1993).

Tiberio, et al., "Self-Assembled Monolayer Electron Beam Resist on GaAs", Anal. Phys. Lett., Feb. 1, 1993.

Vargo, et al., "Monolayer Chem. Lithography and Characterization of Fluoropolymer Films", Langmuir 8, pp. 130-134 (Jan. 20, 1992).

Verpoorte et al., "Three-dimensional micro flow manifolds for miniaturized chemical analysis systems," J. Micromech. Microeng., vol. 4, pp. 246-256, 1994.

Watt, F.M., "Influence of Cell Shape and Adhesiveness on Stratification and Terminal Differentiation of Human Keratinocytes in Culture", J. Cell. Sci. Suppl., 8:313-326, 1987.

Westermark, B., "Growth Control in Miniclones of Human Glial Cells", Exper. Cell Res. 111, pp. 295-299 (Feb. 15, 1978).

Whitesides, et al., "Wet Chemical Approaches to the Characterization of Organic Surfaces: Self-Assembled Monolayers, Wetting, and the Physical-Organic Chemistry of the Solid-Liquid Interface", Langmuir 6, pp. 87-96 (Jan. 31, 1990).

Wilbur, et al., "Microfabrication by Microcontact Printing of Self-Assembled Monolayers", Advanced, Research News, Adv. Mater. (1994) 6, No. 7/8, pp. 600-604 Materials Research News. Adv. Mater. (1994) 6, No. 7/8, pp. 600-604.

Wollman, Eric W., et al., "Photosensitive Self-Assembled Monolayers on Gold: Photochemistry of Surface-Confined Aryl Azide and Cyclopentadienylmanganese Tricarbonyl", J. Am. Chem. Soc., vol. 116, No. 10, pp. 4395-4404 (1994).

Wollman, Eric W., et al., "Scanning Electron Microscopy for Imaging Photopatterned Self-Assembled Monolayers on Gold", Langmuir, vol. 9, No. 6, pp. 1517-1520 (1993).

Wood, A., "Contact Guidance on Microfabricated Substrata: The Response of Teleost Fin Mesenchyme Cells Cells to Repeating Topographical Patterns", J. Cell. Sci., 90:667-681, 1988.

Xia, Younan, et al., "Microcontact Printing of Octadecylsiloxane on the Surface of Silicon Dioxide and Its Application in Microfabrication", Langmuir, pp. 9576-9578 (1995).

DEVICE CONTAINING CYTOPHILIC ISLANDS THAT ADHERE CELLS SEPARATED BY CYTOPHOBIC REGIONS

RELATED APPLICATIONS

This application is a continuation of U.S. patent application Ser. No. 11/331,849, filed Jan. 13, 2006 now U.S. Pat. No. 7,410,791, which is a continuation of U.S. patent application Ser. No. 10/032,280, filed Dec. 21, 2001, now U.S. Pat. No. 7,067,306, which is a continuation of U.S. patent application Ser. No. 09/373,334, filed Aug. 12, 1999, now U.S. Pat. No. 6,368,838, which is a continuation of U.S. patent application Ser. No. 08/951,886, issued as U.S. Pat. No. 5,976,826, filed Oct. 16, 1997, which is a continuation of U.S. patent application Ser. No. 08/659,537, filed Jun. 6, 1996, now U.S. Pat. No. 5,776,748, which is a continuation of U.S. patent application Ser. No. 08/131,838 filed Oct. 4, 1993 now abandoned.

This invention was made with government support NSF Grant Number EEC-880-3014, NIH Grant Number GM30367, ONR Grant Number N00014-86-K-0756, and ACS Grant Number CD-493. The government has certain rights to the invention.

FIELD OF THE INVENTION

The present invention relates generally to derivatization and patterning of surfaces, more particularly to the formation on surfaces of patterns of self-assembled molecular monolayers with differing bioadhesive properties using a microstamp, novel articles produced thereby, and uses therefor.

BACKGROUND OF THE INVENTION

In the field of microelectronic devices and sensors, the development of devices that are small relative to the state of the art, conveniently and relatively inexpensively reproduced, and produced with a relatively low failure rate has long been important. In the fields of cellular and developmental, and molecular biology, microbiology, biomedical devices, and biotechnology, there is now a growing need for devices of similar scale with features as small as or smaller than individual cells.

In the electronics industries, such devices have been produced by a variety of methods. A well-known method of production of such devices is photolithography. According to this technique, a thin film of conducting, insulating, or semiconducting material is deposited on a substrate and a negative or positive resist (photoresist) is coated onto the exposed surface of the material. The resist is then irradiated in a predetermined pattern, and irradiated (positive resist) or non-irradiated (negative resist) portions of the resist are washed from the surface to produce a predetermined pattern of resist on the surface. Alternatively, micromachining has been employed to mechanically remove small areas from a surface to form a pattern.

While the above-described irradiative lithographic methods may be advantageous in many circumstances, all require relatively sophisticated and expensive apparatus to reproduce a particular material pattern on a plurality of substrates, and are relatively time-consuming. Additionally, no method of patterning other than on a flat substrate is commonly available according to the methods.

These techniques have recently been employed in the biological sciences to create patterned surfaces on which cells may be adhered and grown. For example, the orientation, spreading, and shape of several cell types have been shown to be affected by topography. Thus cells have been grown on grooved surfaces which have been created by micromachining surfaces or by using photolithography to etch away parts of surfaces. (See, for example, D. M. Brunette, Exp. Cell Res., 167:203-217, 1986; T. Inoue, et al., J. Biomedical Materials Res., 21:107-126, 1987; B. Chehroudi, et al., J. Biomedical Materials Res., 22:459-473, 1988; G. A. Dunn and A. F. Brown, J. Cell Sci., 83:313-340, 1986; A. Wood, J. Cell Sci., 90:667-681, 1988; B. Chehroudi, et al., J. Biomedical Materials Res., 24-1203-1219, 1990; P. Clark, et al. Development, 99:439-448, 1987.

A need exists in the art for a convenient, inexpensive, and reproducible method of plating or etching a surface according to a predetermined pattern. The method would ideally find use on planar or nonplanar surfaces, and would result in patterns having features in the submicron domain. Additionally, the method would ideally provide for convenient reproduction of existing patterns.

The study of self-assembled monolayers (SAMs) is an area of significant scientific research. Such monolayers are typically formed of molecules each having a functional group that selectively attaches to a particular surface, the remainder of each molecule interacting with neighboring molecules in the monolayer to form a relatively ordered array. Such SAMs have been formed on a variety of substrates including metals, silicon dioxide, gallium arsenide, and others. SAMs have been applied to surfaces in predetermined patterns in a variety of ways including simple flooding of a surface and more sophisticated methods such as irradiative patterning.

Monolayers may be produced with varying characteristics and with various functional groups at the free end of the molecules which form the SAM. Thus, SAMs may be formed which are generally hydrophobic or hydrophilic, generally cytophobic or cytophilic, or generally biophobic or biophilic. Additionally, SAMs with very specific binding affinities can be produced. This allows for the production of patterned SAMs which will adhere cells, proteins, or other biological materials in specific and predetermined patterns.

Accordingly, a general purpose of the present invention is to provide a method of conveniently and reproducibly producing a variety of SAM patterns on planar as well as nonplanar surfaces, the patterns having resolution in the submicron domain and being capable of adhering cells, proteins, or other biological materials in specific and predetermined patterns. Another purpose of the invention is to provide a method of forming a template from an existing pattern having micron or submicron-domain features, the template conveniently reproducing the pre-existing pattern.

SUMMARY OF THE INVENTION

The invention provides novel devices useful for adhering cells in specific and predetermined positions. Such devices are useful in a wide array of cellular biology applications, including cell culturing, recombinant protein production, cytometry, toxicology, cell screening, microinjection, immobilization of cells, influencing the state of differentiation of a cell including promoting differentiation, arresting differentiation or causing dedifferentiation. The devices of the invention also can be used to promote ordered cell-cell contact or to bring cells close to one another, but prevent such contact. The devices of the invention also are useful in the creation of artificial tissues for research or in vivo purposes and in connection with creating artificial organs such as artificial liver devices. The devices also are useful in connection with generating surfaces for prosthetic or implantable devices.

According to one aspect of the invention, a plate defining a surface with a cytophilic island is provided. The cytophilic island includes a self-assembled monolayer. In one preferred embodiment, the device includes a plurality of such islands. These islands can be isolated by a cytophobic region including a self-assembled monolayer, which can be contiguous with the cytophilic island.

According to another aspect of the invention, the plate has a surface with a cytophilic island, wherein the cytophilic island is isolated by a cytophobic region including a self-assembled monolayer, which can be contiguous with the cytophilic island. Again, preferred devices include a plurality of such islands.

Islands of the foregoing type can take on virtually any shape when manufactured according to the methods of the invention, including elongated shapes. They also can be adapted to bind only selected cell types. Preferred islands are between 1 and 2,500 square microns, preferably between 1 and 500 square microns. In some applications, the islands can have an area of as little as between 1 and 100 square microns. Also according to the invention, the islands may have a lateral dimension of between 0.2 and 10 microns. According to another aspect of the invention, the plate has a surface and a pair of cytophilic regions. Each of the cytophilic regions includes a self-assembled monolayer. One of the pair has its self-assembled monolayer modified so as to bind a first cell type but not a second cell type, and the other of the pair has its self-assembled monolayer modified so as to bind the second cell type but not the first cell type. Such cytophilic regions can be positioned to promote or prevent cell-cell contact. They in particular can be adapted to prevent cell-cell contact, but be close enough so they permit cell-cell communication via secreted molecules such as cytokines.

The invention in its broadest aspects including methods and products useful in manufacturing the devices will be described in greater detail below.

DETAILED DESCRIPTION OF THE INVENTION

Figure 1:
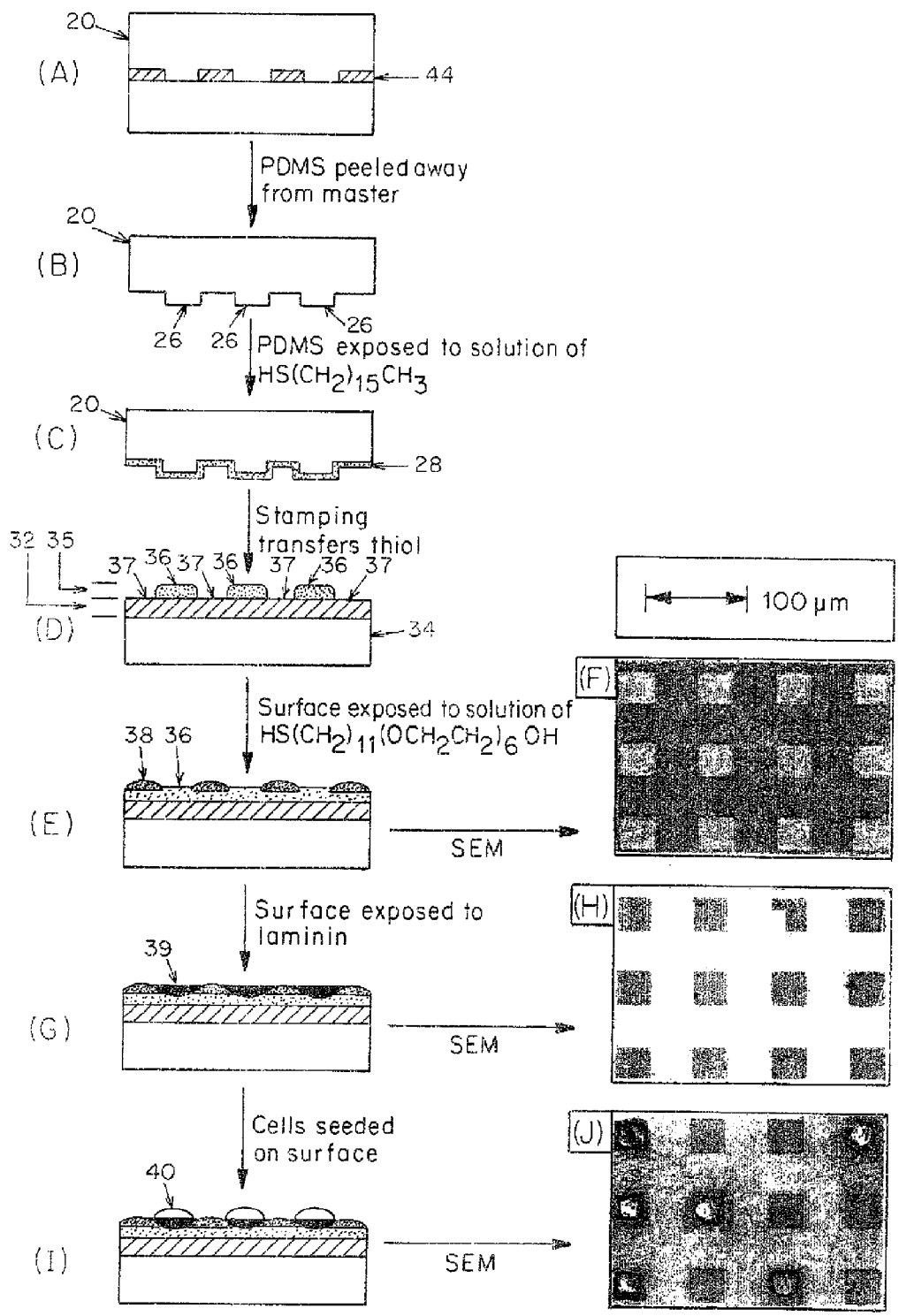
FIG. 1 is a schematic illustration of the stamping process of the present invention and one potential embodiment, including photocopies of scanning electron microscopy (SEM) figures of an exemplary stamping surface, a SAM pattern formed according to the inventive process, and cells adhered to specific and predetermined sites on one of the plates of the present invention.

The present invention provides a method for producing patterned surfaces for plating cells, proteins, or other biological materials in a specific and predetermined pattern. In particular, it provides a method of producing plates with patterned regions of material capable of binding cells, proteins or other biological materials, interspersed with regions of material incapable of binding such biological samples. Significantly, the present invention provides for the production of patterned plates in which the dimensions of the features or details of the patterns may be as small as 0.2-1 µm.

The invention derives from a general new method of creating patterned surfaces applicable in a variety of fields. The method is simple and provides for relatively inexpensive production of many copies of the patterned surface. Applications of the method relating to the production of microelectronic devices are described in U.S. patent application Ser. No. 08/131,841 filed by Kumar and Whitesides on Oct. 4, 1993 and entitled "Formation of Microstamped Patterns on Surfaces and Derivative Articles", the disclosure of which is incorporated herein by reference.

The patterns of the present invention are formed by self-assembled monolayers (SAMs) of organic molecules which spontaneously chemisorb to the surface of a plate. The SAM patterns are applied to the plate using a stamp in a "printing" process in which the "ink" consists of a solution including a compound capable of chemisorbing to form a SAM. The ink is applied to the surface of a plate using the stamp and deposits a SAM on the plate in a pattern determined by the pattern on the stamp. The plate may be stamped repeatedly with the same or different stamps in various orientations and with the same or different SAM-forming solutions. In addition, after stamping, the portions of the plate which remain bare or uncovered by a SAM may be derivatized. Such derivatization may conveniently include exposure to another solution including a SAM-forming compound. The SAM-forming or derivatizing solutions are chosen such that the regions of the finished plate defined by the patterns differ from each other in their ability to bind biological materials. Thus, for example, a grid pattern may be created in which the square regions of the grid are cytophilic and bind cells but the linear regions of the grid are cytophobic and no cells bind to these regions.

A simple illustration of the general process underlying the present invention is presented in FIG. 1. FIG. 1(a) shows an polymeric material 20 cast onto a mold with raised features 44 defining a pattern. FIG. 1(b) shows the stamp 20 with stamping surface 26 after curing and separation from the mold. FIG. 1(c) shows the stamp after inking with an ink 28 including a SAM-forming compound. FIG. 1(d) shows a plate comprising a substrate 34 and a thin coating of surface material 32 after stamping. The SAM forming compound of the ink has chemisorbed to the material surface 32 to form a SAM 35 with surface regions 36 in a pattern corresponding to the stamping surface 26 of the stamp 20. FIG. 1(e) shows the plate after exposure to a second or filling solution including a SAM-forming compound. The second solution has filled the bare regions 37 of the surface material 32 with a second or filling SAM 38. FIG. 1(f) shows an electron micrograph of the surface of a typical plate formed in a grid pattern as shown according to the steps represented in FIG. 1(a) through FIG. 1(e). FIG. 1(g) shows an plate with a patterned SAM on which a material 39 has selectively bound to the surface regions 36 of the first SAM 35. FIG. 1(h) is an electron micrograph of the grid patterned SAM of FIG. 1(f) after exposure to a protein which bound only to the square islands. FIG. 1(i) shows a SAM on which a material 39 has bound to the surface 36 of a SAM and cells 40 have bound to the material 39. FIG. 1(j) shows an electron micrograph of a SAM with cells bound at specific and predetermined positions.

The mold used to form the stamp may be a commercially available item such as a transmission electron microscopy grid or any other corrugated material possessing a pattern which is desired to be reproduced on the stamp. Alternatively, the mold may be especially prepared by any of a variety of methods known in the art. According to one, the mold surface is micromachined from a material such as metal. According to another, the mold surface is formed lithographically by providing a substrate, depositing a film of material onto the substrate, coating an exposed surface of the material with resist, irradiating the resist according to a predetermined pattern, removing irradiated portions of the resist from the material surface, contacting the material surface with a reactant selected to react chemically therewith and selected to be chemically inert with respect to the resist such that portions of the material according to the predetermined pattern are degraded, removing the degraded portions, and removing the resist to uncover portions of the material formed according to the predetermined pattern to form the mold surface. Negative or positive resist may be used, and the procedure adjusted accordingly. According to another method of forming a mold surface, a substrate may be provided, and coated with resist. Then portions of the resist may be irradiated according to a particular predetermined pattern. Irradiated portions of the resist may then be removed from the substrate to expose portions of the substrate surface according to the predetermined pattern, and the substrate may be contacted with a plating reagent such that exposed portions according to the predetermined pattern are plated. Then, the resist may be removed to uncover portions of the exposed substrate according to the predetermined pattern bordered by plated portions of the substrate to form the mold surface.

As noted above, however, any corrugated material may be used as a mold to form the stamps of the present invention.

The stamp is produced by casting a polymeric material onto a mold having the desired pattern. The particular material chosen for formation of the stamp is not critical to the present invention, but should be chosen so as to satisfy certain physical characteristics. The stamp is advantageously chosen to be elastic, such that the stamping surface may very closely conform to minute irregularities in the surface material of the plate to be stamped and to completely transfer the ink thereto, and so as to be amenable to transferring SAMs to nonplanar surfaces. The stamp should not, however, be so elastic as to greatly deform in shape during stamping as this will cause a blurring of the desired pattern. The stamp should also be formed such that the stamping surface comprises an absorbent material selected to absorb SAM-forming solutions. The material may also be swellable. Such swelling and absorbing characteristics serve the important function of providing good definition of an isolated SAM on the surface material of the plate. For example, if a dimensional feature of the stamping surface includes a substantially square-shaped feature, the stamping surface should transfer a SAM-forming compound to the surface material of the plate so as to form SAMs mirroring the substantially square features of the stamping surface, without blurring. Such blurring results from selection of a stamp which does not absorb the ink. When such a stamp is employed, the ink resides as a liquid on the stamping surface, rather than partially or fully within the stamping surface, and when the stamping surface contacts the surface material of a plate, the ink is dispersed from under the stamping surface. According to the stamp of the present invention, however, the ink is dry both on and within the stamping surface. The ink may be dried by simple exposure to air or, if desired, an air current may be provided by a blower or jet. Thus, the ink is absorbed into the stamping surface, dries, and when the stamping surface contacts the surface material of a plate, the ink is not dispersed, but binds to the plate, and the removal of the stamping surface from the surface material of the plate results in well-defined SAM features.

Additionally, the stamp should be fabricated such that the stamping surface is free of any leachable materials such as plasticizers that would interfere with or contaminate the ink. For example, if additives are included in the material used to fabricate the stamp, such additives should be bound to the internal structure of the stamp. For example, if the stamp is fabricated from a polymeric material, any additives should be bound to the polymer backbone thereof.

Material selected for use in fabrication of the stamp is advantageously selected so as not to undergo substantial shape changes when the stamp is formed. For example, when a hardenable fluid is brought into contact with the mold and is hardened, little or no shape change should take place upon such hardening. Thus, any shape changes of features of the stamping surface should be within tolerable limits of precision for formation of SAM features transferred to the surface material of the plate by the stamping surface. If any shape changes do occur upon hardening of the material selected for fabrication of the stamp, it may be desirable that such changes involve miniaturization of the stamping surface features.

According to a preferred embodiment, the stamp is formed from a polymeric material. Polymeric materials suitable for use in the fabrication of the stamp may have linear or branched backbones, and may be crosslinked or non-crosslinked, depending upon the particular polymer and the degree of formability desired of the stamp. A variety of elastomeric polymeric materials are suitable for such fabrication, especially polymers of the general classes of silicone polymers and epoxy polymers. Epoxy polymers are characterized by the presence of a three-member cyclic ether group commonly referred to as an epoxy group, 1,2-epoxide, or oxirane. For example, diglycidyl ethers of bisphenol A may be used, in addition to compounds based on aromatic amine, triazine, and cycloaliphatic backbones. Another example includes the well-known Novolac polymers.

Examples of silicone elastomers suitable for use as the stamp include those formed from precursors including the chlorosilanes such as methylchlorosilanes, ethylchlorosilanes, and phenylchlorosilanes, and the like. A particularly preferred silicone elastomer is polydimethylsiloxane (PDMS). This material has produced better stamps than polyethylene or polystyrene, which were insufficiently elastic, and polybutadiene, which was too elastic.

In addition to the above-described methods for forming the stamp, a photolytic method may be employed in the present invention. For example, a mask may be positioned between a surface and a source of irradiation, and the surface irradiated through the mask for a predetermined period of time. Portions of the surface may be degraded by such irradiation, forming indentations in the surface upon removal of such degraded portions, and thereby defining a stamping surface. According to this method, a variety of patterns may be very conveniently formed in a stamp according to a variety of available masks. In addition, the photolytic method may be used in combination with the above-described methods involving hardening a hardenable fluid on a mold surface. For example, a hardenable fluid may be contacted with a mold surface and allowed to harden to form a stamp having a first predetermined stamping surface, and then the first predetermined stamping surface is irradiated through a mask to create additional features in the stamping surface.

The stamp includes a stamping surface having a variety of features defined by the border between the stamping surface and indentations in the surface. According to the invention, the stamping surface may include features having a variety of lateral dimensions, including very large lateral dimensions for transferring a large SAM to a surface. According to some embodiments of the invention, however, it is highly advantageous to fabricate stamping surfaces so as to have at least one feature with a lateral dimension of less than about 100 microns so as to be able to produce SAMs capable of binding single cells or narrow bands of biological materials such as proteins. According to other embodiments, the stamping surface may include at least one feature with a lateral dimension of less than about 50 microns, less than about 10 microns, less than about 5 microns, less than about 1 micron, or less than about 0.25 microns.

The stamp is inked with a solution capable of forming a SAM by chemisorption to a surface. The inking may, for example, be accomplished by (1) contacting the stamp with a piece of lint-free paper moistened with the ink, (2) pouring the ink directly onto the stamp or (3) applying the ink to the stamp with a cotton swab. The ink is then allowed to dry on the stamp or is blown dry so that no ink in liquid form, which may cause blurring, remains on the stamp. The SAM-forming compound may be very rapidly transferred to the stamping surface. For example, contacting the stamping surface with the compound for a period of time of approximately 2 seconds is generally adequate to effect sufficient transfer, or contact may be maintained for substantially longer periods of time. The SAM-forming compound may be dissolved in a solvent for such transfer, and this is often advantageous in the present invention. Any organic solvent within which the compound dissolves may be employed but, preferably, one is chosen which aids in the absorption of the SAM-forming compound by the stamping surface. Thus, for example, ethanol, THF, acetone, diethyl ether, toluene, isooctane and the like may be employed. For use with a PDMS stamp, ethanol is particularly preferred, and toluene and isooctane and not preferred as they are not well absorbed. The concentration of the SAM-forming compound in the ink solution may be as low as 1 µM. A concentration of 1-10 mM is preferred and concentrations above 100 mM are not recommended.

The plate is then contacted with the stamp such that the inked stamping surface bearing the pattern contacts the surface material of the plate. This may be accomplished by hand with the application of slight finger pressure or by a mechanical device. The stamp and plate need not be held in contact for an extended period; contact times between 1 second and 1 hour result in apparently identical patterns for hexadecanethiol (1-10 mM in ethanol) ink applied to a plate with a gold surface. During contact, the SAM-forming compound of the ink reacts with the surface of the plate such that, when the stamp is gently removed, a SAM is chemisorbed to the plate in a pattern corresponding to the stamp.

As used herein, a "plate" means any object with a surface capable of reacting with a solution including a SAM-forming compound such that a SAM is formed on the surface. The plate may be flat as in a tissue culture plate or glass slide. The plate may also, however, be corrugated, rugose, concave, convex or any combination of these. The plate may also be a prosthetic or implantable device on which it is desired to form a SAM or adhere patterns of cells, proteins, or other biological materials. The word "plate" is used only for expository brevity and is not to be construed as limiting the scope or claims of the present invention to planar surfaces.

A variety of compounds may be used in solution as the ink and a variety of materials may provide the surface material onto which the ink is stamped and the SAM is formed. In general, the choice of ink will depend on the surface material to be stamped. In general, the surface material and SAM-forming compound are selected such that the SAM-forming compound terminates at a first end in a functional group that binds or chemisorbs to the surface of the surface material. As used herein, the terminology "end" of a compound is meant to include both the physical terminus of a molecule as well as any portion of a molecule available for forming a bond with the surface in a way that the compound can form a SAM. The compound may comprise a molecule having first and second terminal ends, separated by a spacer portion, the first terminal end comprising a first functional group selected to bond to the surface material of the plate, and the second terminal end optionally including a second functional group selected to provide a SAM on the material surface having a desirable exposed functionality. The spacer portion of the molecule may be selected to provide a particular thickness of the resultant SAM, as well as to facilitate SAM formation. Although SAMs of the present invention may vary in thickness, as described below, SAMs having a thickness of less than about 50 Angstroms are generally preferred, more preferably those having a thickness of less than about 30 Angstroms and more preferably those having a thickness of less than about 15 Angstroms. These dimensions are generally dictated by the selection of the compound and in particular the spacer portion thereof.

A wide variety of surface materials and SAM-forming compounds are suitable for use in the present invention. A non-limiting exemplary list of combinations of surface materials and functional groups which will bind to those surface materials follows. Although the following list categorizes certain preferred materials with certain preferred functional groups which firmly bind thereto, many of the following functional groups would be suitable for use with exemplary materials with which they are not categorized, and any and all such combinations are within the scope of the present invention. Preferred materials for use as the surface material include metals such as gold, silver, copper, cadmium, zinc, palladium, platinum, mercury, lead, iron, chromium, manganese, tungsten, and any alloys of the above when employed with sulfur-containing functional groups such as thiols, sulfides, disulfides, and the like; doped or undoped silicon employed with silanes and chlorosilanes; metal oxides such as silica, alumina, quartz, glass, and the like employed with carboxylic acids; platinum and palladium employed with nitrites and isonitriles; and copper employed with hydroxamic acids. Additional suitable functional groups include acid chlorides, anhydrides, sulfonyl groups, phosphoryl groups, hydroxyl groups and amino acid groups. Additional surface materials include germanium, gallium, arsenic, and gallium arsenide. Additionally, epoxy compounds, polysulfone compounds, plastics and other polymers may find use as the surface material in the present invention. Polymers used to form bioerodable articles, including but not limited to polyanhydrides, and polylactic and polyglycolic acids, are also suitable. Additional materials and functional groups suitable for use in the present invention can be found in U.S. Pat. No. 5,079,600, issued Jan. 7, 1992, and incorporated herein by reference.

According to a particularly preferred embodiment, a combination of gold as the surface material and a SAM-forming compound having at least one sulfur-containing functional group such as a thiol, sulfide, or disulfide is selected.

The SAM-forming compound may terminate in a second end, opposite to the end bearing the functional group selected to bind to the surface material, with any of a variety of functionalities. That is, the compound may include a functionality that, when the compound forms a SAM on the surface material, is exposed. Such a functionality may be selected to create a SAM that is hydrophobic, hydrophilic, that selectively binds various biological or other chemical species, or the like. For example, ionic, nonionic, polar, nonpolar, halogenated, alkyl, aryl or other functionalities may exist at the exposed portion of the compound. A non-limiting, exemplary list of such functional groups includes those described above with respect to the functional group for attachment to the surface material in addition to:

—OH, —CONH—, —CONHCO—, —NH$_2$, —NH—, —COOH, —COOR, —CSNH—, —NO$_2^-$, —SO$_2^-$, —RCOR—, —RCSR—, —RSR, —ROR—, —PO$_4^{-3}$, —OSO$_3^{-2}$, —SO$_3^-$, —NH$_x$R$_{4-x}^+$, —COO$^-$, —SOO$^-$, —RSOR—, —CONR$_2$, —(OCH$_2$CH$_2$)$_n$OH (where n=1-20, preferably 1-8), —CH$_3$, —PO$_3$H$^-$, -2-imidazole, —N(CH$_3$)$_2$, —NR$_2$, —PO$_3$H$_2$, —CN, —(CF$_2$)$_n$CF$_3$ (where n=1-20, preferably 1-8), olefins, and the like. In the above list, R is hydrogen or an organic group such as a hydrocarbon or fluorinated hydrocarbon. As used herein, the term "hydrocarbon" includes alkyl, alkenyl, alkynyl, cycloalkyl, aryl, alkaryl, aralkyl, and the like. The hydrocarbon group may, for example, comprise methyl, propenyl, ethynyl, cyclohexyl, phenyl, tolyl, and benzyl groups. The term "fluorinated hydrocarbon" is meant to refer to fluorinated derivatives of the above-described hydrocarbon groups.

In addition, the functional group may be chosen from a wide variety of compounds or fragments thereof which will render the SAM generally or specifically "biophilic" as those terms are defined below. Generally biophilic functional groups are those that would generally promote the binding, adherence, or adsorption of biological materials such as, for example, intact cells, fractionated cells, cellular organelles, proteins, lipids, polysaccharides, simple carbohydrates, complex carbohydrates, and/or nucleic acids. Generally biophilic functional groups include hydrophobic groups or alkyl groups with charged moieties such as —COO$^-$, —PO$_3$H$^-$ or 2-imidazolo groups, and compounds or fragments of compounds such as extracellular matrix proteins, fibronectin, collagen, laminin, serum albumin, polygalactose, sialic acid, and various lectin binding sugars. Specifically biophilic functional groups are those that selectively or preferentially bind, adhere or adsorb a specific type or types of biological material so as, for example, to identify or isolate the specific material from a mixture of materials. Specific biophilic materials include antibodies or fragments of antibodies and their antigens, cell surface receptors and their ligands, nucleic acid sequences and many others that are known to those of ordinary skill in the art. The choice of an appropriate biophilic functional group depends on considerations of the biological material sought to be bound, the affinity of the binding required, availability, facility of ease, effect on the ability of the SAM-forming compound to effectively form a SAM, and cost. Such a choice is within the knowledge, ability and discretion of one of ordinary skill in the art.

Alternatively, the functional group may be chosen from a wide variety of compounds or fragments thereof which will render the SAM "biophobic" as that term is defined below. Biophobic SAMs are those with a generally low affinity for binding, adhering, or adsorbing biological materials such as, for example, intact cells, fractionated cells, cellular organelles, proteins, lipids, polysaccharides, simple carbohydrates, complex carbohydrates, and/or nucleic acids. Biophobic functional groups include polar but uncharged groups including unsaturated hydrocarbons. A particularly preferred biophobic functional group is polyethylene glycol (PEG).

The central portion of the molecules comprising the SAM-forming compound generally includes a spacer functionality connecting the functional group selected to bind the to surface material and the exposed functionality. Alternately, the spacer may essentially comprise the exposed functionality, if no particular functional group is selected other than the spacer. Any spacer that does not disrupt SAM packing and that allows the SAM layer to be somewhat impermeable to various reagents such as etching reagents, as described below, in addition to organic or aqueous environments, is suitable. The spacer may be polar; non-polar; halogenated or, in particular, fluorinated; positively charged; negatively charged; or uncharged. For example, a saturated or unsaturated, linear or branched alkyl, aryl, or other hydrocarbon spacer may be used.

A variety of lengths of the SAM-forming compound may be employed in the present invention. If two or more different SAM-forming compounds are used in one stamping step, for example if two or more different SAM-forming compounds are used in the ink, it is often advantageous that these species have similar lengths. However, when a two or more step process is used in which a first SAM is provided on a surface and at least a second SAM is provided on the surface, the various SAMs being continuous or noncontinuous, it may be advantageous in some circumstances to select molecular species for formation of the various SAMs that have different lengths. For example, if the SAM formed by stamping has a first molecular length and the SAM subsequently derivatized to the surface has a second molecular length greater than that of the stamped SAM, a continuous SAM having a plurality of "wells" results. These wells are the result of the stamped SAM being surrounded by the second SAM having a longer chain length. Such wells may be advantageously fabricated according to certain embodiments, for example, when it is desirable to add greater lateral stability to particular biological materials, such as cells, which have been captured in the wells. Such wells may also form the basis for reaction vessels.

Additionally, SAMs formed on the surface material may be modified after such formation for a variety of purposes. For example, a SAM-forming compound may be deposited on the surface material in a SAM, the compound having an exposed functionality including a protecting group which may be removed to effect further modification of the SAM. For example, a photoremovable protecting group may be used, the group being advantageously selected such that it may be removed without disturbance of the SAM of which it is a part. For example, a protective group may be selected from a wide variety of positive light-reactive groups preferably including nitroaromatic compounds such as o-nitrobenzyl derivatives or benzylsulfonyl. Photoremovable protective groups are described in, for example, U.S. Pat. No. 5,143,854, issued Sep. 1, 1992, and incorporated herein by reference, as well as an article by Patchornik, JACS, 92, 6333 (1970) and Amit et al., JOC, 39, 192, (1974), both of which are incorporated herein by reference. Alternately, a reactive group may be provided on an exposed portion of a SAM that may be activated or deactivated by electron beam lithography, x-ray lithography, or any other radiation. Such protections and deprotections may aid in chemical or physical modification of an existing surface-bound SAM, for example in lengthening existing molecular species forming the SAM. Such modification is described in U.S. Pat. No. 5,143,857, referenced above.

The preferred surface portions are cytophilic, that is, adapted to promote cell attachment. Molecular entities creating cytophilic surfaces are well known to these of ordinary skill in the art and include antigens, antibodies, cell adhesion molecules, extracellular matrix molecules such as laminin, fibronectin, synthetic peptides, carbohydrates and the like.

The surface material of the plate may comprise the entire plate onto which the patterned SAMs of the present invention are chemisorbed, or may be a thin film deposited upon a substrate. Where a separate substrate is employed, it may comprise any biological, non-biological, organic, or inorganic material, or a combination of any of these existing as particles, strands, precipitates, gels, sheets, tubing, spheres, containers, capillaries, pads, slices, films, slides, etc. Generally, the substrate of the present invention is substantially planar, although it need not be according to certain embodiments. The substrate may be formed of a conductive, non-conductive, semiconducting material, or the like, and may comprise glass, silica, alumina, plastic or other organic polymers including acrylonitrile-butadiene-styrene copolymers, polysulfone, metals, as well as bioerodable polymers including polyanhydrides or polylactic or polyglycolic acids, or any of the above materials described with respect to the surface material of the present invention. The substrate may additionally include a bonding layer, for example a thin titanium film, to promote adhesion between the surface material and the substrate.

The surface material is generally of a thickness on the order of 500 microns, but may be substantially thicker or may be substantially thinner. For example, when a substrate as a base material is employed, the surface material may have a thickness of less than about 100 nanometers, less than about 10 nanometers, or even less than about 6 nanometers. When a very thin film of surface material is employed, and a transparent substrate supports the surface material, a transparent base support for a SAM results, and this may be advantageous in standard light or electron microscopic or spectrophotometric detection or analysis of any biological material interacting with a SAM on the surface material.

Now that a detailed description of the process for producing patterned plates for plating cells, proteins, and other biological materials has been provided, a variety of particular preferred embodiments relating to particular plate patterns and their uses are disclosed below. These embodiments are intended to be illustrative and are not intended to limit the uses to which the plates of the present invention may be applied.

In a first series of embodiments, a patterned plate is produced with biophilic "islands." By "islands", as used herein, is meant regions of biophilic SAM surrounded by biophobic SAM. Thus, islands on a plate are regions to which cells, proteins or other biological materials may be expected to adhere or bind. Islands may be of any size or shape, including rectilinear, circular, ovoid and arbitrary shapes. In some preferred embodiments, islands are of such area and shape so as to permit binding of only a single cell of a given type or types. In other embodiments, as described below, islands may be shaped or sized so as to create desired patterns of a multiplicity of adhered cells in contact with one another on a given island but separated from and not in contact with cells on a different island. Irrespective of the shape of the islands, a pattern consisting of an array of islands is referred to herein as a grid pattern.

As noted above, the same plate may be stamped several times. In one embodiment, a grid of islands is produced by employing a stamp consisting of a pattern of parallel lines. This stamp may be contacted with the plate a first time in a first orientation and then, after reinking the stamp if necessary, either the stamp or the plate is rotated through some angle and contacted a second time in a second orientation. If the angle of rotation is 90°, a square grid pattern may be produced.

After the desired SAM pattern has been formed on the plate, the portion of the plate's surface which is bare or not covered by the stamped SAM may be derivatized by exposing it to a second or "filling" solution with characteristics differing from the first solution which was used as the ink. This exposure may be accomplished by dipping the plate in a bath of solution, by pouring the solution onto the plate or by any other convenient method which does not disrupt the patterned SAM. The second solution may form a SAM over the surface of the plate which is not already covered by the patterned SAM of the ink. That is, the second of filling solution may contain a second or "filling" SAM-forming compound which will form a second or "filling" SAM on the bare portions of the plate's surface. The result is a plate completely covered by complementary patterns of two or more SAMs of differing properties.

In this embodiment of forming a grid pattern, the ink used in the stamping can form a biophobic SAM or it can be modified in situ after SAM formation to form a biophobic SAM by reacting the functional groups at the free ends of the SAM with a compound that will make it biophobic. The filling solution, which derivatizes the areas of the plate corresponding to the islands, can form a biophilic SAM or it can be modified in situ after SAM formation to form a biophilic SAM by reacting the functional groups at the free ends of the SAM with a compound that will make it biophilic.

In an alternative embodiment, the raised stamping surface of the stamp may correspond to the islands and the ink will form a SAM which is biophilic or may be made biophilic by modifying the functional groups at the free ends of the SAM. In this embodiment, the filling solution which derivatizes the bare regions of the surface material can form a biophobic filling SAM or may be modified so as to become biophobic. In this embodiment, round, oval or arbitrarily shaped, in addition to square or rectangular islands may be produced.

It is not necessary in all embodiments to derivatize any bare portions of the surface remaining after forming patterned SAMs. Depending upon the surface used, the bare surface may have the desired biophilic or biophobic characteristics and, thus, the filling step may be omitted. When it is desired that cells adhere to a bare portion of some surfaces, the provision of serum facilitates this binding.

In one set of preferred embodiments of a patterned plate with a grid pattern, the islands are of a size and shape appropriate for binding individual cells and are separated one from another by a sufficiently large area of biophobic SAM so as to prevent cell-to-cell contact. The islands of these plates are designed so as to be of a size less than or approximately commensurate with the cells to be studied when the cells have adhered. As is well known to one of ordinary skill in the art, cells in suspension will generally flatten upon adhering to a surface. Also, as in known in the art, cells vary in the degree to which they flatten upon binding. White blood cells, for example, have a diameter of approximately 20 µm whereas *Xenopus laevis* oocytes may have a diameter of 1 mm. Relative to other cells, these cells do not flatten substantially. On the other hand, most other cells, and particularly epithelial cells, spread and flatten to a greater degree. Endothelial cells for example, may have an area of approximately 250-4,000 square µm, whereas hepatocytes may have an area of approximately 500-10,000 square µm. And, even within a given cell type, a wide range of sizes may be found. The appropriate size, therefore, is generally determined empirically. Beginning with an island size roughly commensurate with the projected size of the cells when bound, it is well within the ability of one of ordinary skill in the art to vary the island size to determine a size appropriate to the intended use without undue experimentation. This is most easily accomplished by beginning with a plate bearing islands of varying sizes, contacting the plate with a suspension of cells, and then determining which size or sizes of islands appropriately bound cells. The size of the islands should be chosen such that it is not so large as to admit binding of more than one cell per island. In some circumstances, such as when it is desired to remove the cells by elution or for replica plating, a smaller size may be chosen so that the cells have less contact area with the biophilic SAM and are more easily removed. The islands should not, however, be so small as to render cell adhesion unlikely.

In an alternative set of embodiments, the islands are chosen so as to admit binding of a number of cells such that the cells may form cell-to-cell contacts. The size of the islands, however, is chosen so as to prevent formation of a large sheet of cells which would be subject to cell retraction or detachment, or the formation of spheroid and/or trabecular structures of cells.

As is known to those of skill in the art, certain classes of cells, specialized epithelial cells in particular and especially anchorage dependent and polar cells, are affected by their binding to a substrate or their contacts with other cells. Thus, the viability, growth, proliferation, differentiation, orientation and spreading of certain cells have been shown to depend on the substrate to which the cells are adhered (D. Gospodarowicz, et al., *Cancer Res.*, 38:4155-4171, 1978; J. Folkman and A. Moscona, *Nature*, 273:345-349, 1978; A. Ben Ze'ev. et al., *Cell*, 21:365-372, 1980; D. E. Ingber, et al., *In Vitro Cell Dev. Biol.*, 23:387-394, 1987; D. E. Ingber and J. Folkman, *J. Cell Biol.*, 109:317-330, 1989). The growth and viability of anchorage dependent cells, for example, may be different when they are allowed to become more extended or flattened than when the cells are maintained in a rounded form or in suspension. Similarly, for fibroblast growth factor (FGF) stimulated capillary endothelial cells, it has been demonstrated that by altering the density of extracellular matrix (ECM) attachment sites, cell shape is altered and the cells may be switched between growth and differentiation modes in vitro (D. E. Ingber and J. Folkman, *J. Cell Biol.*, 109:317-330, 1989). It has also been shown that cell-to-cell contact or cell anchorage may affect cellular processes such as post-translational modification of proteins (e.g. D. Kabat, et al., J. Cell Biol., 101:2274-2283, 1985).

Thus, the present invention also provides for patterned plates of cells with altered or controlled viability, growth, proliferation, differentiation, protein processing, orientation, and/or spreading characteristics.

Cells may be shaped using plates with islands of varying shapes which are sufficiently large to bind only a single cell and which will cause the adhered cell to conform to that shape of the island. In this way, a cell which normally flattens or extends may be forced to remain in a rounded form. Alternatively, although an island may admit of binding more than one cell, the island may be shaped such that it is relatively narrow in one dimension and forces the cells adhered to it to form a single line of cells, each of which has been forced into an elongated shape. The chosen area and shape of the island will depend upon the particular cells and uses intended and, in light of the present disclosure, is within the ability and discretion of one of ordinary skill in the art.

Alternatively, when cell-to-cell contact or anchorage in a more flattened or extended form is desired in order to affect the viability, growth, proliferation, differentiation, protein processing, orientation, and/or spreading characteristics of cells, but large sheets of cells are not desired because they are subject to detachment from the surface of the culture plate, islands admitting of more than one cell may be used such that the cells establish the desired cell-to-cell contacts but do not form large sheets. In this embodiment, the islands are chosen to be of a sufficient size to adhere a desired number of cells but are separated from other islands by biophobic regions which are sufficiently wide to prevent cells from bridging them. Such an embodiment is particularly preferred for use in cultures in which the cells are kept or frequently washed with serum free media, as for example in a bioreactor, and cell-to-cell contact is desired because of its effect on the cells' viability, growth, proliferation, differentiation, protein processing, orientation, and/or spreading characteristics. Bioreactors include various devices for maintaining cultures such as perfusion systems such as Cube System (Costar), T-Flasks such as the Falcon models (Bectin-Dickinson), roller bottle culture systems, and stirred tanks or spinner flasks with cells adhered to microcarriers or beads. The use of the plates of the present invention in bioreactors is particularly contemplated.

In another embodiment of the invention using patterned plates with a grid pattern, the plates are employed in cytometry. For example, the numbers or ratios of different types of cells in a sample may be efficiently assayed by contacting the suspension with one of the plates of the present invention, allowing a period of time for the cells to bind, washing away any excess solution or unbound cells if necessary, and then identifying and counting the different cell types at the specific and predetermined locations of the biophilic islands. Because the size of the islands may be chosen such that no more than one cell may bind on any given island, because the locations and geometric pattern of the islands may be predetermined, and because the cells will remain at fixed locations during the cell counting, the patterned plates of the present invention provide for much greater efficiency and accuracy in cytometry.

In a particularly preferred embodiment in cytometry, the cells are identified and counted by an automated detector unit. Because the locations and geometric patterns of the islands are predetermined, the detector can be designed or programmed to take measurements specifically at those locations. The presence or absence of a cell on an island or the nature of the cell may be detected by any of a variety of known fluorescence or spectrophotometric assays based upon binding of fluorescently labeled antibodies or other ligands, cell size or morphology, or by the cells' spectrophotometric transmission, reflection or absorption characteristics either with or without biological staining. Standard light or electron microscopy can also be employed. The detector unit is positioned either above or below the plate. In the case of fluorescence assays, a detector unit may be placed above the plate or, if the plate is translucent, below the plate. In the case of transmission spectrophotometric assays, a translucent plate is used, a source of electromagnetic radiation is placed on one side of the plate and a detector unit on the other. Because of the small distances between individual isolated cells permitted by the present invention, detectors employing fiber optics are particularly preferred. Such sources of electromagnetic radiation and such detectors for electromagnetic transmission, reflection or emission are known in the applicable art and are readily adaptable for use with the invention disclosed herein.

In one preferred embodiment of the assays described above, the detector unit consists of a multiplicity of individual detectors in an array corresponding spatially to the islands of the plate such that the entire detector unit may be positioned above or below the plate and the individual detectors each measure electromagnetic radiation transmitted through or emitted or reflected from a particular island on the plate. In this embodiment, the number and type of a great many individual cells may be individually assessed simultaneously with minimal human labor or involvement. In another embodiment, the detector unit consists of a single detector which may be sequentially positioned over each island to measure the electromagnetic emission or transmission of each cell, alternatively, or the plate may be moved to position each island under the detector sequentially. Preferably, this sequential positioning is automated and, in a most preferred embodiment, the detector is programmable such that it may be employed with plates of varying dimensions and varied spacing between islands. The design of such automated detectors is well within the ability of one of ordinary skill in the applicable art.

When an automated detector unit is employed, a standard or control plate may also be provided. Such a plate would contain islands including islands to which no cells are bound so that a reference would be provided and the detector would recognize such islands. In addition, islands bearing cells of known types could be provided to act as references to allow the detector unit to classify the cells on a subject plate. Furthermore, depending upon the biophilic SAM which is chosen, cells of different types may adhere to the plate with differing affinities. Thus, depending upon the cells to be studied and the biophilic SAM employed, a standard cytometric method may be employed on a sample first and then the plates and method of the present invention may be employed on the same or a substantially similar sample to calibrate the system.

In addition, when only a subset of cells in a sample are of interest, for example, the white blood cells in a blood sample containing both red and white blood cells, a specifically biophilic SAM may be chosen that will selectively bind the cells of interest and, subsequent to binding, the extraneous cells may be washed away. Given a particular set or subset of cells to be studied, the choice of a biophilic SAM specific to those cells is within the ability of one of ordinary skill in the art and, given the disclosures herein, one of ordinary skill in the art is enabled to produce appropriate patterned biophilic SAMs specific for those cells.

Merely by means of example, and without limiting the scope of the present invention, the following cytometric applications of the present invention are listed. The cytometry system provided by the present invention could be used in measuring the numbers and types of cells in blood, urine, cerebrospinal fluid, PAP smear, biopsy, ground water, sea water, riparian water, and reservoir water samples, and any other application in which there is a desire to determine the presence, number or relative frequency of one or more types of cells in a large sample of cells.

In another aspect of the present invention, a method of assaying the effects of various treatments and compounds on individual cells is provided. In particular, the invention provides the capability to assay the effects of various treatments or compounds on each of a great many individual cells plated at high density but separated from each other and at fixed locations on the plate. In this embodiment of the invention, many cells are applied in suspension to the plates of the present invention.

Once the suspension of cells has been applied to the plate, a period of time is allowed to elapse in order to allow the cells to bind to the islands. Excess fluid including unbound cells may be washed away. The cells may then be subjected to a treatment or exposed to a compound in situ on the plate or, in some situations, the cells may be pre-treated before being introduced to the plate for binding. The effects of the treatment or compound on each cell may then be individually assayed in a manner appropriate to the cell type and the treatment or compound being studied. For example, the effects of treatments or compounds potentially capable of affecting cell morphology may be assayed by standard light or electron microscopy. Alternatively, the effects of treatments or compounds potentially affecting the expression of cell surface proteins may be assayed by exposing the cells to either fluorescently labeled ligands of the proteins or antibodies to the proteins and then measuring the fluorescent emissions associated with each cell on the plate. As another example, the effects of treatments or compounds which potentially alter the pH or levels of various ions within cells may be assayed using various dyes which change in color at determined pH values or in the presence of particular ions. The use of such dyes is well known in the art. For cells which have been transformed or transfected with a genetic marker, such as the β-galactosidase, alkaline phosphatase, or luciferase genes, the effects of treatments or compounds may be assessed by assays for expression of that marker and, in particular, the marker may be chosen so as to cause spectrophotometrically assayable changes associated with its expression.

In particularly preferred embodiments, the assay is spectrophotometric and automated. In these embodiments, the treatment or compound potentially causes a change in the spectrophotometric emissions, reflection or absorption of the cells. A detector unit, as described above, may be employed. Because of the small distances between individual isolated cells permitted by the present invention, detectors employing fiber optics are particularly preferred. Such sources of electromagnetic radiation and such detectors for electromagnetic transmission, reflection or emission are known in the applicable art and are readily adaptable for use with the invention disclosed herein.

In one preferred embodiment of the assays described above, the detector unit consists of a multiplicity of individual detectors in an array corresponding spatially to the islands of the plate, as described above. In this embodiment, the effect of a treatment or compound on a great many individual cells may be individually assessed simultaneously with minimal human labor or involvement.

In particularly preferred embodiments, a suspension of cells is applied to one of the plates of the present invention in which the biophilic SAM is chosen so as to selectively or preferentially bind a certain type or types of cells. The cells are subjected to a treatment or exposed to a compound which will potentially cause a change in the electromagnetic emission, reflection or transmission characteristics of the cells and an automated detector unit records the emission, reflection or transmission characteristics of each cell individually by assaying electromagnetic emission, reflection or transmission at points corresponding to each island on the plate.

When an automated detector unit is used, a plate which has not been exposed to any cells may be used as a control before testing the experimental plate to provide reference values to exclude from the results islands on the experimental plates which have been exposed to cells but which have not bound cells.

In another particularly preferred embodiment, plates upon which cells have been allowed to bind are assayed prior to any potentially effective treatment or compound and then treated or exposed. As the cells maintain their individual positions on the plates, a second assay may be performed to detect changes in the assay results on a cell-by-cell basis after treatment or exposure. Such a two-step assay is particularly appropriate for treatments or compounds which potentially cause cell toxicity or disrupt binding.

The above described embodiments, employing the plates of the present invention which allow for plating individual cells at high density but with little or no overlap or contact of cells, can be employed for high through-put tests of potentially useful treatments including radiation and pharmacological or toxicological compounds. In particular, the present invention provides assays which allow assays both as to qualitative and quantitative changes in individual cells and quantitative assays as to percentages of cells affected by any given treatment or compound.

In a different embodiment, the present invention provides means for identifying individual cells which have been successfully transformed or transfected with recombinant DNA technology. A culture of cells exposed to transforming or transfecting vectors, including plasmids, phasmids, cosmids, retroviruses and various homologous recombination or integration elements, may be plated on the plates of the present invention to separate the cells and cause them to bind individually at the locations of the islands on the plate. Individual cells which have been transformed or transfected may then be identified by the methods described above or other methods well known to those of ordinary skill in the art. Particularly simple, given the disclosures herein, is the identification of individual cells transformed or transfected with a vector including a marker locus which causes a spectrophotometrically detectable change in a cell's function, metabolism, gene expression or morphology. Marker loci may also be included which cause cells to exhibit a sensitivity or resistance to a particular treatment or compound. Cells transformed or transfected by such vectors may be first selected on the basis of the appropriate sensitivity or resistance and then plated as individual cells and further selected or characterized by the methods and employing the plates described herein. In particular, selection may be employed prior to plating on the plates of the present invention to isolate transformed or transfected cells and then the cells may be assayed in situ using the presently disclosed materials and methods to identify and isolate cells with, for example, particularly high or low expression of the characteristic to which the transformation or transfection was directed.

In a particularly preferred embodiment, an automated detector unit, as described above, is employed.

In a different embodiment, the present invention provides materials and methods for retrieving individual cells which are bound to the plates of the present invention. That is, the present invention provides for materials and methods for isolating and manipulating particular individual cells which are present on a plate containing a great multiplicity of cells separated one from another by only a few microns.

In one embodiment, cells are plated to a primary plate with each island of the plate capable of binding a single cell. A secondary plate, bearing an island with an appropriate biophilic SAM only at a position corresponding spatially to the position of the island bearing the desired cell may then be contacted with the cell on the primary plate. The desired cell may then adhere to the secondary plate such that, when the secondary plate is drawn away from the primary plate, the desired cell and only the desired cell adheres to the secondary plate. Thus, the individual desired cell is retrieved for purposes which may include growth for a DNA or cDNA library, growth into a tissue culture, or in the case of transformed or transfected oocytes, uterine implantation and growth into a transgenic organism. The secondary plates of the present invention may be custom made to retrieve a particular cell by means of the stamp production methods disclosed herein, or may be pre-made. If, for example, plates of a particular dimension with islands positioned at standard points are employed on a regular basis, secondary plates for retrieval of cells bound at particular islands may be prepared in advance. Thus, for a plate with 100 islands in a 10×10 array, 100 secondary plates may be prepared in advance for retrieval of an individual cell at any one of the 100 possible island positions. More efficiently, 25 secondary plates may be prepared in advance to contact with any of the four 5×5 quadrants of a 10×10 primary plate. Even more efficiently, if the pattern is symmetrical, a lesser number of secondary plates capable of rotation may be produced. In addition, secondary plates could be produced which would retrieve more than one cell by constructing a secondary plate with biophilic SAM islands corresponding spatially to more than one island on the primary plate. Further, to enhance transfer of the desired cell or cells from the primary plate to the secondary plate, it may be desirable to have larger islands of biophilic SAM on the secondary plate or to use a biophilic SAM on the secondary plate with a higher binding affinity for the desired cell or cells than the biophilic SAM on the primary plate.

In another embodiment of a cell retrieval system, an automated system provides for the contacting of a secondary plate with a specified island of a primary plate such that a desired cell is transferred from the primary to the secondary plate. Thus, a desired cell is identified by the coordinates of the position of the island to which it is bound and a secondary plate, consisting of a single island is positioned over the coordinates of the desired cell on the primary plate and the secondary plate is contacted with the desired cell to allow transfer of the desired cell from the primary to the secondary plate. As above, the size of the island or the nature of the biophilic SAM on the secondary plate may be chosen so as to enhance the efficiency of transfer of the desired cell from the primary to the secondary plate. In a particularly preferred embodiment, the detection of the desired cells is by means of an automated detector unit and the coordinates of the desired cells are transmitted from the detector unit to an automated retrieval unit such that human labor and involvement are minimized.

Given the disclosures of the present invention for isolating individual cells on islands at predetermined positions on one of the disclosed plates, the design and production of a cell retrieval unit is within the ability of one of ordinary skill in the applicable art. Absent the present disclosure, retrieval of a particular individual cell from amongst a high density plate of a great many cells would be an arduous and difficult task. The binding of individual cells to particularly defined positions on the plates of the present invention, however, provides for a method of such retrieval. Such a cell retrieval system may be employed, for example, to retrieve transformed or transfected cells, potentially cancerous cells in a PAP smear or biopsy, or fertilized eggs adhered to the patterned plates of the present invention.

In another aspect of the present invention, patterned plates and a method are provided for immobilizing cells for microinjection. As is known in the art, microinjection of, for example, dyes, proteins, and DNA or RNA sequences, is made more difficult when the cells to be microinjected are not immobilized on a substrate and/or localized at specific and predetermined positions. By providing the patterned plates and methods disclosed herein, the present invention greatly simplifies the microinjection process. Thus, in light of the present disclosure, patterned plates with biophilic islands which can bind a given type or types of cells can be produced and the type or types of cells can be bound individually to specific and predetermined locations on the plates. Cell types which may be sought to be bound include bacterial cells such as *Escherichia* and *Pseudomonas* species; mammalian cells such as chinese hamster ovary (CHO), baby hamster kidney (BHK), COS, human fibroblast, hematopoietic stem cells, and hybridoma cell lines; yeast; fingi; and cell lines useful for expression systems such as yeast or *Xenopus laevis* oocytes. The listing above is by no means intended to be exhaustive but is merely exemplary of the sorts of cells which may be immobilized to specific and predetermined positions for microinjection. Subsequent to microinjection, the cells may be assayed for functional expression or transformation on the plates of the present invention with the detectors described herein and, if desired, individually retrieved with the retrieval system disclosed herein.

In another aspect of the present invention, materials and methods are provided which allow for the immobilization of oocytes at specific and predetermined positions for in vitro fertilization techniques. That is, the patterned plates of the present invention allow for immobilization of oocytes, including human oocytes, at specific and predetermined positions. These immobilized oocytes may then be contacted in situ on the plates with a solution including sperm cells potentially capable of fertilizing the oocytes. The fertilized oocytes, or zygotes, may then be conveniently identified because of their fixed positions on the plates of the present invention and individually retrieved for implantation or storage by standard methods or the methods disclosed herein. As will be obvious to one of ordinary skill in the art, the biophilic SAM for immobilizing the oocytes/zygotes can be chosen from a wide array of potential SAMs ranging from generally biophilic or hydrophobic SAMs to SAMs including moieties, including antibodies, which specifically bind the oocytes/zygotes involved in the in vitro fertilization process. Subsequent to exposure to the sperm solution, the cells may be assayed for successful fertilization on the plates of the present invention with the detectors described herein and, if desired, individually retrieved with the retrieval system disclosed herein.

In another aspect of the present invention, patterned plates are provided which may be used to bind or adsorb proteins in specific and predetermined patterns.

As is known to those of ordinary skill in the art, phenomena associated with the adsorption of proteins to solid synthetic materials are important in many areas of biotechnology including, for example, production, storage and delivery of pharmaceutical proteins, purification of proteins by chromatography, design of biosensors and prosthetic devices, and production of supports for attached tissue culture (see, for example, *ACS Symposium Series* 343, T. A. Horbett and J. L. Brash, Eds., Am. Chem. Soc., Washington, D.C., 1987; J. D. Andrade, *Surface and Interfacial Aspects of Biomedical Polymers: Protein Adsorption*, Plenum Press, NY, 1985; *Materials Research Society Proceedings* 252, L. G. Cima and E. Ron, Eds., Mat. Res. Soc., Pittsburgh, Pa., 1992). A number of researchers have demonstrated the formation of patterns of proteins (see, for example, A. S. Lea, et al., *Langmuir* 8:68-73, 1992). But these have typically relied on photolithography to create the patterns (see, for example, S. K. Bhatia, et al., *J. Am. Chem. Soc.*, 114:4432-4433, 1992; S. K. Bhatia, et al., *Anal. Biochem.*, 208:197-205, 1993). The patterned plates of the present invention provide for relatively inexpensive and efficient patterning of proteins with features of the pattern as small as 0.2-1 μm which are useful in these applications.

In this embodiment, a plate is created with patterned SAMs according to the methods disclosed above. Depending upon the desired application, the pattern may include islands or parallel rows of SAMs with different properties. One SAM may be biophilic and the other may be biophobic as applied or they may be chemically modified as described above so as to become biophilic or biophobic subsequent to SAM formation. In an alternative embodiment, as described above, two SAMs may be patterned onto a plate, one of which is biophilic and one of which is biophobic and, subsequent to binding a protein or proteins to the biophilic SAM, the biophobic SAM may be chemically modified so as to become biophobic. In this way, a second protein or group of proteins may be bound to the previously biophobic but now biophilic SAM to create a pattern of two or more protein groups. Similarly, patterns of more than two SAMs may be used to create more complicated patterns of proteins in accordance with the present invention.

For protein adsorption, particularly preferred biophilic SAMs are those comprised of ω-functionalized alkanethiols ($HS(CH_2)_nR$) where the R group is a non-polar (e.g., $R=CH_3$) or ionic (e.g., $R=CO_2^-$, $PO_3H^-$, or 2-imidazolo) group. Particularly preferred biophobic SAMs are ω-functionalized alkanethiols ($HS(CH_2)_nR$) in which the R group is a polar but non-ionic group such as oligo (ethylene glycol)-terminated thiols (e.g., $R=(OCH_2CH_2)_6OH$).

Patterned proteins which have been patterned according to the materials and methods of the present invention may be transferred from the patterned plates of the present invention by contacting the plates with other biophilic or bioadhesive substrates, well known in the art, without disrupting the patterns and then be used in a variety of applications. Thus, for example, the surfaces of prosthetic or implanted devices or tissue culture plates can be patterned with the patterned proteins produced by the present invention. Alternatively, such devices may be directly stamped with the SAM patterns of the present invention and the proteins patterned directly upon them.

In a different embodiment of the present invention, the patterned plates provided herein may be used to produce plates with cells growing in desired patterns and to control the growth, proliferation, differentiation, orientation and/or spreading of certain classes of cells.

As in the previously described embodiments of the present invention, depending upon the intended use, an enormous variety of patterns may be produced and a multiplicity of stamps and/or a multiplicity of SAMs may be employed to create patterns of one or more types of cells. As before, the SAMs may be generally or specifically biophilic or biophobic as applied or may be subsequently modified to become generally or specifically biophilic or biophobic after SAM formation by chemical modification of functional groups at the free ends of the SAM-forming compounds. In particular, when several SAMs are present in a pattern but only one is biophilic, a first type of cell may be adhered to the biophilic SAM and then one of the remaining biophobic SAMs may be chemically modified in situ so as to become biophilic. A second cell type may then be adhered to the newly biophilic SAM and this process can be repeated to create a complex pattern of different cell types.

In another embodiment, a plate with patterned proteins may be prepared as described above and cells may then be allowed to adhere to the patterned proteins to form a plate of patterned cells. In particularly preferred embodiments, the proteins are extracellular matrix proteins such as collagen, fibronectin or laminin; or are specific cell receptors such as integrins. In these embodiments, then, the patterned protein mediates the cell adhesion to form patterned cells. Alternatively, a patterned plate of biophilic and biophobic SAMs may be created and a wide variety of non-protein compounds may first be adhered to the pattern to mediate cell binding. Such compounds include but are not limited to sialic acid, lectins, polygalactose and other carbohydrates.

The patterned plates of the present invention may be used to create patterns of cells in which cells are isolated on islands to prevent cell to cell contact, in which different types of cells are specifically brought into contact or in which cells of one or more types are brought into a pattern which corresponds to the pattern or architecture found in natural tissue.

Such plates of patterned cells have a wide variety of applications which will be apparent to one of ordinary skill in the art and all such applications are intended to fall within the scope of this invention. Particularly preferred applications include but are not limited to use in bioreactors for the production of proteins or antibodies, especially by recombinant cells; use in tissue culture; use for the creation of artificial tissues for grafting or implantation; use in artificial organs such as artificial liver devices for providing liver function in cases of liver failure; and use for generating artificial tissues to adhere to the surfaces of prosthetic or implantable devices to prevent connective tissue encapsulation.

In another embodiment particular different types of cells may be brought together on the same plate. For example, in the toxicological assays described above, it may be desired to plate a percentage of hepatocytes on the plate to convert potentially procarcinogenic compounds into carcinogenic compounds and to assay the effects on other nonhepatocyte cells on the same plate.

In another embodiment of the present invention, specific cell to cell contacts can be patterned by using a plate with island-like biophilic regions which are connected by biophilic bridge-like regions but are otherwise surrounded by biophobic material. Such a "bridged island" plate would have application, for example, in creating patterned neural cells with neural processes making contacts only along specific and predetermined bridge regions.

In a different embodiment of the invention, the present invention may provide one or more microcultures of determinable volume, and specific and predetermined positions on a plate. For example, if the free ends of a first SAM-forming compound are hydrophilic and the free ends of a second SAM-forming compound are hydrophobic, and these compounds are used to form a patterned plate in which there are small islands of the hydrophilic SAM, a plurality of droplets of aqueous fluid may be placed on these islands. With knowledge of the surface area of the islands, and the surface tension of the aqueous fluid and hydrophobicity and hydrophilicity of the islands and surrounding SAM (measured, for example, by contact angle), the volume of the droplets may be determined. Thus, if the volume of the droplet microcultures is known and/or can be controlled, and the concentration of compounds within the microcultures can be controlled, then individual cells, including bacteria, yeast, and mammalian, as well as spores and other microorganisms can be cultured in these microcultures. Such a microculture may be used in the same means and with the same assays and detector and retrieval units as described above. In addition, however, such microcultures are particularly useful for assays for compounds that are secreted from cells. Because the cells are isolated in their own microcultures, such compounds do not diffuse away or mix with compounds secreted by other cells in nearby but isolated microcultures.

The methods and materials, function and advantage of these and other embodiments of the present invention will be more fully understood from the examples below. The following examples are intended to illustrate the benefits of the present invention, but do not exemplify the full scope of the invention.

Example 1

Preparing a Mold and Stamp

A mold according to the present invention was fabricated. A template consisting of an exposed and developed photoresist pattern on silicon is prepared (This type of fabrication is described in any conventional photolithography text, such as *Introduction to Microelectronic Fabrication*, by Richard C. Jaeger, Gerold W. Neudeck and Robert F. Pierret, eds., Addison-Wesley, 1989). Templates such as electron microscopy grids or other corrugated materials may also be used. The template is placed in a container such as a petri dish. A 10:1 (w:w or v:v) mixture of PDMS-Sylgard Silicone Elastomer 184 and Sylgard Curing Agent 184 (Dow Corning Corp., Midland, Mich.) was poured into the petri dish. It was not necessary to put the mixture of PDMS-elastomer and curing agent under vacuum to remove dissolved dioxygen. The PDMS cured at room temperature in the laboratory ambient for 30 to 60 min. This cure was followed by additional curing at 65° C. for approximately one hour or until the polymer was rigid. After cooling to room temperature, the PDMS-stamp was carefully peeled from the template.

Example 2

Preparation of Plates with Metallic Surfaces

Gold films (~2000 Å thick) were prepared by electron-beam evaporation of gold (Materials Research Corp., Orangeburg, N.Y.; 99.999%) onto single-crystal silicon (100) test wafers (Silicon Sense, Nashua, N.H.; 100 mm dia., ~500 μm thick) that had been precoated with a film of titanium (Johnson Mathey, 99.99%; ~50 Å thick) that acted as an adhesion promoter between the silicon oxide and the gold. The silicon wafers coated with gold were fractured into square plates (~2 cm×2 cm) and used in the formation of the various types of patterned SAM plates.

Example 3

Preparing a Patterned Plate with a Grid Pattern

A stamp fabricated in accordance with Example 1 was fabricated. The stamp was fabricated so as to have a linear indentation pattern contiguous with a liner stamping surface pattern. That is, the stamp had an array of indentational lines separating stamping surface lines. The surface was coated with hexadecanethiol in ethanol using a cotton swab. The stamp was applied to a smooth gold surface, and removed. The resultant pattern included parallel SAM lines of 2 microns in width. After removal of the stamp, the stamping surface was re-coated and rotated approximately 45° to a second orientation, and re-applied to the surface. A grid pattern resulted.

Example 4

Patterned Proteins

Several patterned SAM plates were prepared by first forming patterns of $HS(CH_2)_{15}CH_3$ on gold using a rubber stamp made of polydimethylsiloxane. The remaining, underivatized surface of the gold was derivatized with a second SAM by placing the patterned plate in a second solution containing $HS(CH_2)_{11}EG_6OH$ (10 mM in ethanol) for 10 s. The sample was rinsed with heptane and with ethanol and dried under a stream of dry nitrogen.

Buffer solutions for protein adsorption were prepared from potassium dihydrogen phosphate (0.01 M) and titrated to pH 7.5 with sodium hydroxide (0.1 M). Briefly, the protocol for effecting adsorption of proteins involved the immersion of plates with patterned SAMs in solutions of the protein of interest in phosphate buffer at room temperature. After the desired time of immersion, the plate was removed from the solution and rinsed with distilled, deionized water and dried under a stream of nitrogen. To pattern an adsorbed protein, it was desirable to use a modification of the protocol of Horbett, (Horbett, T. A. in *Techniques of Biocompatibility Testing* Vol. II, pp. 183-214, Williams, D. F., Ed., CRC Press Inc. Boca Raton, Fla., 1986; Rapoza, R. J. and Horbett, T. A. *J. Coll. Interface Sci.*, 136:480-493, 1990), and first to place the patterned SAM plate in buffer and then to add concentrated protein solution so that the final, total concentration of protein in the solution in contact with the patterned SAM plate was that desired for adsorption (e.g., 1 mg/mL). This procedure eliminated the exposure of the SAM to the interface of the solution of protein and air. After the appropriate adsorption time, the solution of protein was displaced with at least five equivalent volumes of distilled deionized water. The samples were further rinsed directly with distilled deionized water and dried under a stream of nitrogen.

Example 5

Patterned Plating of Primary Rat Hepatocytes

Mold patterns were developed using a computer program commonly used for integrated circuit designs. The pattern was created on a glass plate coated with photosensitive emulsion using a pattern generator (Gyrex 1005A). The final mask was made by contact printing the emulsion plate onto a chromium-coated quartz plate. Silicon wafers were cleaned in piranha solution, rinsed with distilled water and dehydrated under $N_2$ at 200° C. for 8 hrs. One layer (1-2 μm) of negative photoresist (Union Carbide) was spin-coated on the silicon wafers. The coated wafers were baked at 90° C. for 30 min, placed in a mask aligner (Karl Zuss, Munich, Germany), and exposed to ultraviolet light through the chromium mask containing the desired pattern. The exposed wafers were hard baked at 120° C. for 90 s and developed to produce the desired photoresist template for the rubber stamp. A 10:1 mixture (v/v or w/w) of Silicone Elastomer-184 and Silicone Elastomer Curing Agent-184 (Dow Corning Corporation) was poured onto this photoresist template, allowed to cure at 60° C. for 45-90 min, and peeled away from the template. The resulting PDMS stamp was inked by brushing it with a cotton swab that had been moistened with a 1 mM solution of a hexadecanethiol ($HS(CH_2)_{15}CH_3$) in ethanol. The inked stamp was then placed in contact with a plate with a gold surface (2000 Angstroms Au on a titanium-primed silicon wafer) to form the SAMs of hexadecanethiolate. Upon removal of the stamp, the plate was washed for 5 s in a solution of an alkanethiol terminated with ethylene glycol oligomer ($HS(CH_2)_{11}(OCH_2CH_2)_6OH$, 1 mM in ethanol). The plate was finally washed with ethanol and dried in a stream of dry nitrogen. Patterned plates were coated with 1 μg/cm² of mouse laminin using a carbonate buffer adsorption method. The laminin adhered to the hexadecanethiol islands but not to the hydrophilic PEG-terminated SAM. Primary rat hepatocytes were isolated and cultured in defined medium on the laminin-coated islands as described in Mooney et al., *J. Cell Physiol.*, 151:497 (1992).

Example 6

Controlling Cell Shape and Function

The ability of the techniques of the present invention to control distribution and shape was explored by plating primary rat hepatocytes in hormonally-defined medium (Mooney et al, Id.) on laminin-coated substrata that were stamped with square and rectangular islands having micron dimensions (5×5 microns to 100×100 microns). Cells attached preferentially to the adhesive, laminin-coated islands and were prevented from extending onto surrounding non-adhesive regions. Selective attachment of cells to these adhesive islands resulted in development of regular arrays of individual adherent cells that were aligned single file in both horizontal and vertical columns, extending over large areas (mm²) of the culture surface. The adhesive islands limited cell spreading and largely prevented cell-cell contact formation, although a few cells (less than 10%) were found to bridge between adjacent islands. In most cases, cells conformed to the shape of the underlying island. Actual projected cell areas, determined by computerized image analysis, were consistently within 20% of the island area. In many cells, the abrupt prevention of cell spreading at the lateral borders of each island resulted in formation of corresponding square and rectangular cells with "corners" that approximated 90 degrees. In contrast, cells plated at the same density on unpatterned, laminin-coated gold substrata spread extensively, formed numerous cell-cell contacts, and exhibited normally pleomorphic shapes. Thus, the shape and spatial distribution of cultured cells could be simply controlled using our "rubber stamp" method to engineer adhesive islands with desired design characteristics and shapes.

Since the extent to which a cell spreads influences its growth and function, maintaining large populations of cells in specific shapes on patterned substrata can be an effective way of controlling both the behavior of individual cells and the performance of the entire culture. By fabricating adhesive islands of varying size on a single substratum, we were able to maintain cells at defined degrees of extension for extended periods of time, independent of the presence of growth factors or the composition mechanics or molecular density of the extracellular matrix. Quantitation of DNA synthesis in hepatocytes cultured on islands of different size in defined medium (Mooney et al., Id.) containing saturating amounts of soluble growth factors (EGF, insulin, and dexamethasone) revealed significant differences in the number of cells that exhibited nuclear labelling. DNA synthesis was highest (60% nuclear labeling index) in cells on unpatterned surfaces where cells could spread without restriction. Decreasing the size of the adhesive islands resulted in a progressive reduction in growth such that less than 3% of the cells adherent to the smallest islands (less than 1600 μm²) entered S phase. This result was not due to changes in cell viability; similar percentages of cells incorporated the vital dye, calcein AM, on all substrata.

We assessed the differentiated function of hepatocytes cultured on substrata coated with uniformly sized islands by assaying the culture supernatant for secretion of albumin, a liver-specific product. Hepatocytes cultured on unpatterned substrata rapidly lost the ability to secrete high levels of albumin. In contrast, hepatocytes maintained near normal levels of albumin secretion for at least 3 days when cultured on the smallest adhesive islands (40×40 μm) that fully restricted cell extension. In general, albumin secretion rates decreased as the size of the adhesive island was increased and growth was promoted. These data are consistent with studies, that show that cells, such as hepatocytes, can be switched between growth and differentiation in the presence of soluble mitogens by modulating cell shape. In past studies, shape was controlled by varying ECM molecular coating densities on otherwise non-adhesive dishes and thereby, altering cell-ECM contact formation. The present results demonstrate that it is the degree to which the cell extends and not the density at which the ECM ligand is presented that indicates whether a cell will grow or differentiate. Use of this type of approach, which relies upon chemically-defined, patterned surfaces and serum-free culture conditions, facilitates further analysis of the basic mechanism of coupling between cell shape and function and of other fundamental biological processes that involve changes in cell form or cell-cell contact formation.

The invention claimed is:

1. A device, comprising:
   a plate defining a surface; and
   a plurality of cytophilic islands on the surface to which cells adhere isolated by cytophobic regions to which cells do not adhere contiguous with the cytophilic islands, wherein the cytophilic islands are arranged in a grid pattern on the plate, and wherein at least one of the cytophilic islands and cytophobic regions is formed of a self-assembled monolayer.

2. A device as in claim 1, wherein at least one of the cytophilic islands is formed of a self-assembled monolayer.

3. A device as in claim 1, wherein at least one of the cytophobic regions is formed of a self-assembled monolayer.

4. A device as in claim 1, wherein at least one of the cytophilic islands is between 1 and 100 square microns.

5. A device as in claim 1, wherein the cytophilic islands adhere one cell type but do not substantially adhere a second cell type different from the first cell type.

6. A device as in claim 1, wherein at least one of the cytophilic islands binds only a selected cell type.

7. A device as in claim 1, wherein the grid pattern comprises a pattern of parallel lines.

8. A device as in claim 1, wherein the surface comprises at least one cell bound to a cytophilic island.

9. A device as in claim 8, wherein the cell has been exposed to a dye.

10. A device as in claim 8, wherein the cell has been exposed to a fluorescently-labeled compound.

11. A device as in claim 8, wherein the cell has been exposed to a treatment or a compound that causes a change in a spectrophotometric emission, reflection or absorption of the cell.

12. A device as in claim 1, comprising a plurality of cells bound to the plurality of cytophilic islands.

13. A device as in claim 1, comprising a plurality of different cell types bound to the plurality of cytophilic islands.

14. A device as in claim 1, comprising a plurality of same cell types bound to the plurality of cytophilic islands.

15. A device as in claim 1, wherein the cytophilic islands are of a size and shape appropriate for binding individual cells on each island.

16. A device as in claim 1, further comprising a detector unit comprising a multiplicity of individual detectors arranged in an array corresponding spatially to the cytophilic islands of the plate.

17. A device as in claim 1, further comprising a detector unit comprising a single detector which may be sequentially positioned over each cytophilic island of the plate.

18. A device as in claim 1, comprising cytophilic islands bearing cells of known types which act as references to allow classification of cells on the plate.

19. A device as in claim 8, wherein the cell is a mammalian cell.

* * * * *